US011225507B2

(12) United States Patent
Cheng et al.

(10) Patent No.: US 11,225,507 B2
(45) Date of Patent: Jan. 18, 2022

(54) CONFORMATION SWITCHABLE ANTIMICROBIAL PEPTIDES AND METHODS OF USING THE SAME

(71) Applicant: THE BOARD OF TRUSTEES OF THE UNIVERSITY OF ILLINOIS, Urbana, IL (US)

(72) Inventors: Jianjun Cheng, Champaign, IL (US); Lin-Feng Chen, Champaign, IL (US); Menghua Xiong, Guangzhou (CN); Yan Bao, Guangzhou (CN)

(73) Assignee: The Board of Trustees of the University of Illinois, Urbana, IL (US)

( * ) Notice: Subject to any disclaimer, the term of this patent is extended or adjusted under 35 U.S.C. 154(b) by 124 days.

(21) Appl. No.: 16/480,914

(22) PCT Filed: Jan. 25, 2018

(86) PCT No.: PCT/US2018/015261
§ 371 (c)(1),
(2) Date: Jul. 25, 2019

(87) PCT Pub. No.: WO2018/140613
PCT Pub. Date: Aug. 2, 2018

(65) Prior Publication Data
US 2020/0399319 A1 Dec. 24, 2020

Related U.S. Application Data

(60) Provisional application No. 62/450,285, filed on Jan. 25, 2017.

(51) Int. Cl.
*C07K 14/00* (2006.01)
*A61K 38/00* (2006.01)
*C07K 1/107* (2006.01)

(52) U.S. Cl.
CPC ............ *C07K 14/001* (2013.01); *A61K 38/00* (2013.01); *C07K 1/1072* (2013.01)

(58) Field of Classification Search
None
See application file for complete search history.

(56) References Cited

U.S. PATENT DOCUMENTS

| | | | |
|---|---|---|---|
| 5,245,056 A | 9/1993 | Karpf et al. | |
| 5,516,758 A | 5/1996 | Stevens et al. | |
| 5,840,833 A | 11/1998 | Kahn | |
| 5,962,410 A | 10/1999 | Jaynes et al. | |
| 6,187,313 B1 | 2/2001 | Segelman | |
| 6,271,198 B1 | 8/2001 | Braisted et al. | |
| 7,049,431 B2 | 5/2006 | Iversen | |
| 7,723,469 B2 | 5/2010 | Walensky et al. | |
| 8,461,316 B1 | 6/2013 | Sung et al. | |
| 10,030,103 B2 * | 7/2018 | Cheng | C08L 77/04 |
| 2003/0119754 A1 | 6/2003 | Lackey et al. | |
| 2004/0063905 A1 | 4/2004 | Aojula et al. | |
| 2006/0287457 A1 | 12/2006 | Nishiguchi et al. | |
| 2006/0292135 A1 | 12/2006 | Loomis et al. | |
| 2010/0291672 A1 | 11/2010 | Takeoka et al. | |
| 2011/0082092 A1 | 4/2011 | Chatterton | |
| 2011/0142767 A1 | 6/2011 | Yanni et al. | |
| 2013/0178421 A1 | 7/2013 | Yu et al. | |
| 2013/0274173 A1 * | 10/2013 | Cheng | A61K 47/595 514/2.4 |
| 2015/0374844 A1 | 12/2015 | Degrado et al. | |

FOREIGN PATENT DOCUMENTS

| | | |
|---|---|---|
| JP | S6396200 A | 4/1988 |
| WO | 2012019121 A2 | 2/2012 |
| WO | 2014126828 A1 | 8/2014 |
| WO | 2016210442 A1 | 12/2016 |

OTHER PUBLICATIONS

International Search Report and Written Opinion dated Apr. 5, 2012 for PCT/US2011/062656, filed on Nov. 30, 2011, 8 pgs.
"Supplementary European Search Report" Application EP 11845856, dated Jan. 14, 2015, 3 pgs.
Amarzguioui, Mohammed et al., "Rational design and in vitro and in vivo delivery of Dicer substrate siRNA," Nature Protocols, Jun. 2006, 508-517, 1.
Aouadi, Myriam et al., "Orally delivered siRNA targeting macrophage Map4k4 suppresses systemic inflammation," Nature, Apr. 2009, 1180-1185, 458.
Bahar et al., "Antimicrobial Peptides," Pharmaceuticals, 6:1543-1575, Nov. 2013.
Beevers et al., "Helical membrane peptides to modulate cell function," Chemical Society Reviews, Mar. 2010. 39: pp. 2146-2157.
Brogden et al., "Will New Generations of Modified Antimicrobial Peptides Improve Their Potential as Pharmaceuticals?" Int. J. of Antimicrobial Agents, 38:217-225, May 2011.
Brogden, "Antimicrobial Peptides: Pore Formers or Metabolic Inhibitors in Bacteria?" Nature, 3:238-250, Mar. 2005.
Chen et al., "Rational Design of α-Helical Antimicrobial Peptides with Enhanced Activities and Specificity/Therapeutic Index," J. Biol. Chem., 280(13):12316-12329, Apr. 2005.
Chin et al., "Biodegradable Broad-Spectrum Antimicrobial Polycarbonates: Investigating the Role of Chemical Structure on Activity and Selectivity," Macromolecules, 46(22):8797-8807, Nov. 2013.
Dong, Lei et al., "Targeting delivery oligonucleotide into macrophages by cationic polysaccharide from Bletilla striata successfully inhibited the expression of TNF-α," Journal of Controlled Release, Mar. 2009, 214-220, 134.
Engler et al., "Effects of Side Group Functionality and Molecular Weight on the Activity of Synthetic Antimicrobial Polypeptides," Biomacromolecules, 12(5):1666-1674, May 2011.

(Continued)

*Primary Examiner* — Fred H Reynolds
(74) *Attorney, Agent, or Firm* — Haukaas Fortius PLLC; Michael H. Haukaas

(57) ABSTRACT

The disclosure provides a class of pH-sensitive, helix/random conformation switchable antimicrobial polypeptide (HRS-AMP) compositions as a single agent to selectively kill bacteria (e.g., *H. pylori*) under acidic condition in the stomach with diminished bacterial resistance compared to currently used antibiotics. Methods of treating bacterial infections in the stomach are also provided.

17 Claims, 14 Drawing Sheets

(56) References Cited

OTHER PUBLICATIONS

Engler et al., "Highly Efficient "Grafting onto" a Polypeptide Backbone Using Click Chemistry," Angew. Chem. Int. Ed., Nov. 2009.4*: pp. 9334-9338.

Gabrielson et al., "Reactive and Bioactive Cationic a-Helical Polypeptide Template for Nonviral Gene Delivery," Angew. Chem. Int. Ed., 51:1143-1147, Jan. 2012.

Gabrielson, Nathan P. et al., "A cell-penetrating Helical Polymer for siRNA Delivery to Mammalian Cells," Molecular Therapy, May 29, 2012, 1599-1609, 20.

Gabrielson, Nathan P. et al., "Multiplexed supramolecular self-assembly for non-viral gene delivery," Biomaterials, Sep. 1, 2010, 9117-9127, 31.

Howard, Kenneth A. et al., "Chitosan/siRNA Nanoparticle-mediated TNF-α Knockdown in Peritoneal Macrophages for Anti-inflammatory Treatment in a Murine Arthritis Model," Molecular Therapy, Jan. 2009, 162-168, 17.

International Search Report and Written Opinion of the ISA/US dated Sep. 22, 2016 in International Application No. PCT/US2016/039657; 6pgs.

International Search Report dated Sep. 12, 2014; Application No. PCT/US14/33888 filed Apr. 11, 2014, 5 pgs.

Itaka et al., "Supramolecular Nanocarrier of siRNA from PEG-Based Block Catiomer Carrying Diamine Side Chain with Distinctive p K a Directed to Enhance Intracellular Gene Silencing," Journal of the American Chemical Society, Oct. 1, 2004. 126: pp. 13612-13613.

Kuhla, Angela et al., "Role of the perforin/granzyme cell death pathway 1n D-Gal/LPS-induced inflammatory liver injury," American Journal of Physiology-Gastrointestinal Liver Physiology, Feb. 2009, G1069-G1076, 296.

Lee et al., "Two Interdependent Mechanisms of Antimicrobial Activity Allow for Efficient Killing in Nylon-3-Based Polymeric Mimics of Innate Immunity Peptides," Biochimica et Biophysica Acta, 1838:2269-2279, Sep. 2014.

Lu et al., "Ionic Polypeptides with Unusual Helical Stability" Nat Commun., 2(206):1-9, Feb. 2011.

Lu et al., "Hexamethyldisilazane-Mediated Controlled Polymerization of a-Amino Acid N-Carboxyanhydrides," J. Am. Chem. Soc., Oct. 2007. 129: pp. 14114-14115.

Luijten et al., "Cross-Linking-Induced Permanently Perpendicular Helix Orientation in Surface-Grafted Polyglutamate Films," Langmuier, Jul. 1, 2007. 23: pp. 8163-8169.

Lundberg, Patric et al., "Protection against TNFα-dependent liver toxicity by intraperitoneal liposome delivered DsiRNA targeting TNFα in vivo," Journal of Controlled Release, Nov. 7, 2011, 194-199, 160.

Ng et al., "Synergistic Co-Delivery of Membrane-Disrupting Polymers with Commercial Antibiotics against Highly Opportunistic Bacteria," Adv Mater., 25(46):6730-6736, Dec. 2013.

Niidome et al., "Chain Length of Cationic a-Helical Peptide Sufficient for Gene Delivery into Cells," Bioconjugate Chem., May 1999. 10: pp. 773-780.

Nowak et al., "Rapidly recovering hydrogel scaffolds from self-assembling diblock copolypeptide amphiphiles," Nature, May 23, 2002. 417: pp. 424-428.

Raguse et al., "Structure-Activity Studies of 14-Helical Antimicrobial P-Peptides: Probing the Relationship between Conformational Stability and Antimicrobial Potency," J Am Chem Soc, 124(43):12774-12785, Oct. 2002.

Sanborn et al., "Extreme Stability of Helices Formed by Water-Soluble Poly-N-Substituted Clycines (Polypeptoids) with a-Chiral Side Chains," Biopolymers, Jan. 2002. 63: pp. 12-20.

Schmidt et al., "Criterion for Amino Acid Composition of Defensins and Antimicrobial Peptides Based on Geometry of Membrane Destabilization," J. Am. Chem. Soc., 133:6720-6727, May 2011.

Song et al., "Polypeptides with Quaternary Phosphonium Side Chains: Synthesis, Characterization, and Cell-Penetrating Properties," Biomacromolecules,15(4):1491-1497, Apr. 2014.

Sonia, T.A. et al., "Chitosan and Its Derivatives for Drug Delivery Perspective," Advances in Polymer Sciences, Apr. 2011, 23-54, 243.

Tang et al., "General Route toward Side-Chain Functionalized a-Helical Polypeptides," Biomacromolecules, May 2010. 11: pp. 1585-1592.

Tang et al., "Helical Poly(arginine) Mimics with Superior Cellpenetrating and Molecular Transporting Properties," Chem. Sci., 4(10):3839-3844, Aug. 2013.

Tejero et al., "High Efficiency Antimicrobial Thiazolium and Triazolium Side-Chain Polymethacrylates Obtained by Controlled Alkylation of the Corresponding Azole Derivatives," Biomacromolecules., 16(6):1844-1854, Jun. 2015.

Un, Keita et al., "Efficient Suppression of Murine Intracellular Adhesion Molecule-1 Using Ultrasound-Responsive and Mannose-Modified Lipoplexes Inhibits Acute Hepatic Inflammation," Hepatology, Jul. 2012, 259-269, 56.

Vaz et al., "Comparison of Design Strategies for Promotion of B-Peptide 14-Helix Stability in Water," Chem. Biochem., Sep. 2008. 9: pp. 2254-2259.

Wang, Hao et al., "A Supramolecular Approach for Preparation of Size-Controlled Nanoparticles," Angewandte Chemie (International ed. in English), May 2009, 4344-4348, 48.

Written Opinion dated Sep. 12, 2014; Application No. PCT/US14/33888 filed Apr. 11, 2014, 11 pgs.

Wyman et al., "Design, Synthesis, and Characterization of a Cationic Peptide That Binds to Nucleic Acids and Permeabilizes Bilayers," Biochemistry, Mar. 11, 1997. 36: pp. 3008-3017.

Xiong et al., "Helical Antimicrobial Polypeptides with Radial Amphiphilicity," Proc Natl Acad Sci U S A., 112(43):13155-13160, Oct. 2015 (with Supporting Information, pp. 35).

Yang et al., "Synthetic Antimicrobial Oligomers Induce a Composition-Dependent Topological Transition in Membranes," J Am Chem Soc., 129(40):12141-12147, Oct. 2007.

Yen et al., "Cationic, Helical polypeptide-based Gene Delivery for IMR-90 Fibroblasts and Human Embryonic Stem Cells," Biomater Sci., 1(7):719-727, Jul. 2013.

Yin et al., "Non-Viral Gene Delivery via Membrane-Penetrating, Mannose-Targeting Supramolecular Self-Assembled Nanocomplexes," Adv Mater., 25(22)13063-3070, Jun. 2013.

Yin et al., "Supramolecular Self-Assembled Nanoparticles Mediate Oral Delivery of Therapeutic TNF-a siRNA against Systemic Inflammation," Angew. Chem. Int. Ed., 52(22)15757-5761, May 2013.

Yin, Lunxiang et al., "Sonochemical Synthesis of Cerium Oxide Nanoparticles—Effect of Additives and Quantum Size Effect," Journal of Colloid and Interface Science, Feb. 2002, 78-84, 246.

Zheng et al., "Maximizing Gene Delivery Efficiencies of Cationic Helical Polypeptides via Balanced Membrane Penetration and Cellular Targeting," Biomaterials 35(4):1302-1314, Jan. 2014.

Yin et al., "Light-Responsive Helical Polypeptides Capable of Reducing Toxicity and Unpacking DNA: Toward Nonviral Gene Delivery," Angew Chem Int Ed Engl., 52(35):9182-9186, Aug. 2013.

* cited by examiner

CONFORMATION SWITCHABLE ANTIMICROBIAL PEPTIDES AND METHODS OF USING THE SAME

RELATED APPLICATIONS

This application is a national stage application, filed under 35 U.S.C. § 371, of International Application No. PCT/US2018/015261, filed Jan. 25, 2018 which claims priority under 35 U.S.C. § 119(e) to U.S. Provisional Patent Application No. 62/450,285 filed Jan. 25, 2017, which applications are incorporated herein by reference.

GOVERNMENT SUPPORT

This invention was made with government support under Grant No. R21AI117080 awarded by the National Institutes of Health and Grant Nos. CHE 1508710 and 1308485 awarded by the National Science Foundation. The government has certain rights in the invention.

BACKGROUND OF THE INVENTION

*Helicobacter pylori*, the main etiological factor for the development of gastritis, gastric ulcers, and gastric carcinoma, infect about 50% of the population worldwide. To eradicate *H. pylori*, triple therapy is recommended as first-line therapy in the clinical setting, which involves the use of a combination of two antibiotics for optimal bacterial killing and a proton pump inhibitor (PPI) for increasing the gastric pH to enhance the antimicrobial activity and stability of antibiotics in the gastric fluid. However, the combination therapy is often associated with various side effects. In particular, it leads to undesired elimination of commensal bacteria, which are closely related to various physiological and metabolic processes, the development of the immune system, and a range of diseases, such as inflammatory bowel disease, colon cancer, Parkinson's disease, obesity, diabetes, atherosclerosis, and allergy. For example, gut microbiota play an important role in colorectal carcinogenesis, and colorectal cancer patients show significantly reduced microbial diversity in feces.

In addition, the efficacy of triple therapy is hindered by the constant increment of drug resistance, and the resistance to any of the three drugs will make the treatment end up with failure. The antimicrobial activity of the antibiotics is often insufficient to eradicate bacteria for the patients that are acid hyper-secretors or extensive metabolizers, wherein PPI fails to increase the gastric pH. To address these critical issues, anti-*H. pylori* therapy should be designed to feature selective killing *H. pylori* with potentially diminished resistance.

Antimicrobial peptides (AMPs) have recently emerged as promising antimicrobial candidates, which are capable of disrupting bacterial membrane structure to combat multi-drug resistant microbes. AMPs can kill *H. pylori* hi vivo as a single agent. However, these antimicrobial agents often suffer from high cytotoxicity (e.g., hemolysis), poor proteolytic stability, and low selectivity. We recently developed a class of radially amphiphilic (RA) antimicrobial polypeptides with a hydrophobic helical core and a charged exterior shell, affording potent antimicrobial activity that are associated with their helical structure. While these RA polypeptides afford several advantages over conventional AMPs, such as simplicity in design and stability against proteases, they lack the capability of differentiating pathogenic bacteria from commensal bacteria, which will cause non-specific killing of commensal bacteria when applied for anti-*H. pylori* therapy.

Accordingly, there is a need for new antibacterial polypeptides that possess properties enabling the differentiated killing of pathogenic bacteria, particularly *H. pylori*, versus commensal bacteria.

SUMMARY

Clinical treatment of *Helicobacter pylori* using combination therapy is greatly challenged by the undesired killing of commensal bacteria and progressive development of drug resistance. To address these issues, we developed pH-sensitive, helix-coil conformation transitionable, antimicrobial polypeptides as a single therapeutic agent to selectively kill *H. pylori* under acidic condition in the stomach with minimal toxicity to commensal bacteria and diminished drug resistance. Through the control of the secondary structure transition, the polypeptides showed unappreciable toxicity to commensal bacteria and tissues at physiological pH when they adopted random coiled conformation, while the restoration of helical structure in the acidic stomach allowed the polypeptide to regain membrane disruptive capability to effectively and selectively kill *H. pylori*, including drug-resistant strains.

The invention therefore provides pH-responsive helix-coil conformation transitionable antimicrobial polypeptides for the selective killing of bacteria such as *Helicobacter pylori*. In one embodiment, the invention provides an antimicrobial polypeptide comprising Formula I:

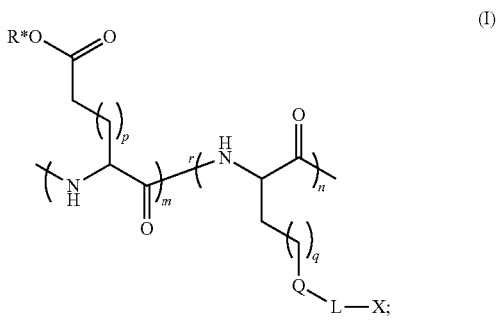

wherein
  m is 3 to about 50;
  n is 5 to about 100;
  p is 0 or 10;
  q is 0, 1, 2, or 3;
  R* is H or a negative charge;
  Q is —C(=O)O—, —C(=O)NH—, —NH—C(=O)—, or a direct bond;
  L is a carbon-containing linker of at least two atoms in length; and
  X is primary amine, a secondary amine, a tertiary amine, or a quaternary ammonium moiety; wherein the polypeptide adopts a random coil confirmation in solution at a pH of greater than about 6.5, and the polypeptide adopts a helical confirmation in solution at a pH of less than about 3.5; and wherein the r between the m and n segments indicates that the polypeptide is a random polymer polypeptide.

L can be, for example, $(C_2\text{-}C_{12})$alkyl, wherein the $(C_2\text{-}C_{12})$alkyl is optionally interrupted with one to five oxygen atoms, sulfur atoms, or a combination thereof, and optionally interrupted with phenyl, cycloalkyl, heterocycle, or heteroaryl.

In certain embodiments, X can be an aliphatic or aromatic quaternary ammonium moiety. In one embodiment, X is —N⁺(R)₃ wherein each R is independently phenyl or a straight chain or branched $(C_1-C_{10})$alkyl. The total number of carbon atoms in the three R groups combined can be 3 to about 15. In certain specific embodiments, X is:

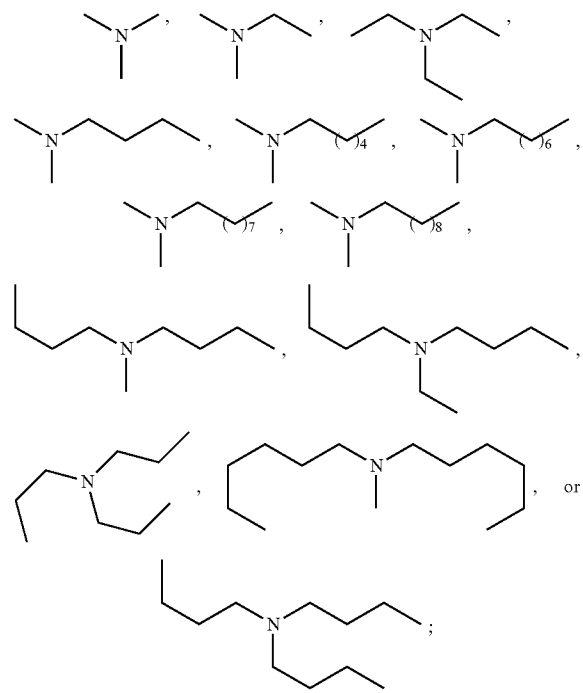

wherein X is bonded to L at the nitrogen of X to form a quaternary ammonium moiety.

In various embodiments, X is an aromatic quaternary ammonium moiety, for example, an aromatic quaternary ammonium moiety selected from:

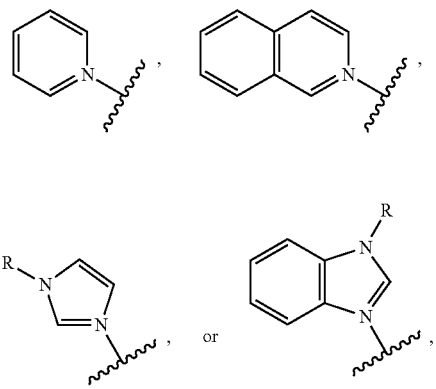

wherein R is H or $(C_1-C_{10})$alkyl.

A polypeptide comprising Formula I can be a polypeptide comprising Formula II:

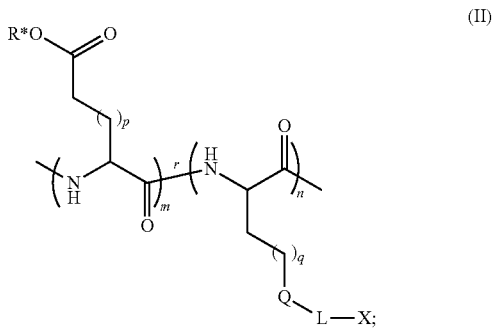

wherein
m is 3 to about 40;
n is 5 to about 80;
p is 0 or 1;
q is 0, 1, 2, or 3;
R* is H or a negative charge;
Q is —C(=O)O—, —C(=O)NH—, —NH—C(=O)—, or a direct bond;
L is a carbon-containing linker of two to twenty atoms in length; and
X is an aliphatic or aromatic quaternary ammonium moiety.

A polypeptide comprising Formula II can be a polypeptide comprising Formula III or Formula IV:

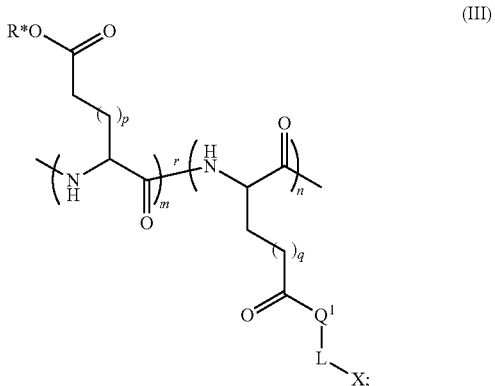

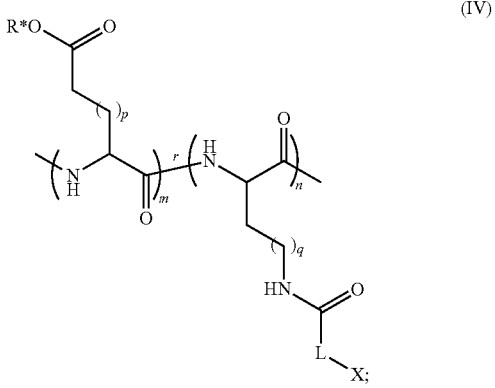

wherein Q¹ is O or NH. In other embodiments, the polypeptide of any one of the formulas above can be a polypeptide comprising Formula V:

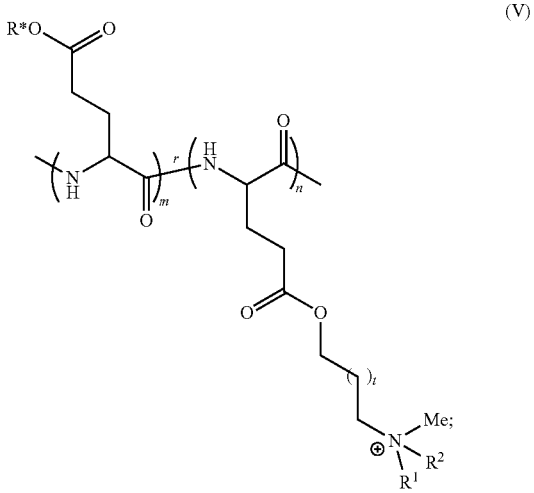

(V)

wherein m is about 3 to about 40, n is about 5 to about 80, t is about 1 to 8, and $R^1$ and $R^2$ are each independently ($C_2$-$C_8$)alkyl.

In each of the embodiments above, L can be, for example, ($C_2$-$C_{12}$)alkyl, —$CH_2$-Ph-($CH_2$)$_y$— wherein y is 1 to about 4, —$CH_2$-Ph-O—($CH_2$)$_2$—O—($CH_2$)$_2$—, —$CH_2$-Ph-O—($CH_2$)$_2$—S—($CH_2$)$_2$—, —$CH_2$-Ph-O—($CH_2$)$_3$—O—($CH_2$)$_2$ —, —$CH_2$-Ph-O—($CH_2$)$_3$—S—($CH_2$)$_2$—, or —$CH_2$-Ph-O—$CH_2$—CH(S($CH_2$)$_2$—X)—$CH_2$—S—($CH_2$)$_2$ —.

The polypeptide has low toxicity at neutral or physiological pH and has high antibacterial activity against *H. pylori* in an environment having a pH of less than about 4.4 (e.g., in the stomach of a mammal). Accordingly, the invention provides a method comprising treating a bacterial infection in the stomach of a subject in need thereof by administering to the subject a therapeutically effective amount of a polypeptide described herein, wherein the bacterial infection is thereby treated. The invention also provides a method of killing *H. pylori* in the stomach of a mammal that has an *H. pylori* infection, the method comprising administering to the infected mammal a therapeutically effective amount of a polypeptide described herein, wherein the *H. pylori* is thereby killed, and wherein commensal bacteria in the intestines are not killed.

In one embodiment, the polypeptide is administered orally.

In one embodiment, the bacterial infection is caused by *H. pylori*.

In one embodiment, the subject has been diagnosed with gastritis, a gastric ulcer, or gastric carcinoma, for example, caused by *H. pylori*.

In one embodiment, the polypeptide causes killing of less than 50% of commensal bacteria in the ileal contents of the subject.

The invention therefore provides novel polymers (e.g., polypeptides) of the formulas described herein, intermediates for the synthesis of the polymers, as well as methods of preparing the polymers. The invention also provides polymers that are useful as intermediates for the synthesis of other useful polymers and compositions. The invention provides for the use of the polymers for the manufacture of medicaments useful for the treatment of bacterial infections in a mammal, such as a human.

The invention further provides for the use of the compositions described herein for use in medical therapy. The medical therapy can be treating a bacterial infection, such as an infection caused by *H. pylori*. The invention also provides for the use of a composition described herein for the manufacture of a medicament to treat such infections. The invention additionally provides for the use of a composition described herein for the inhibition or killing of bacteria in an acidic environment and for the treatment of bacterial infections in the stomach of a subject.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

0, normal; 1, spotty changes in cellular staining characteristics of some surface epithelial cells in an otherwise normal mucosa (mild injury); 2, more generalized changes and/or disruption of the surface epithelium in several areas (moderate injury); 3, extensive mucosal destruction (severe injury). All data are represented as average±SD and analyzed by student's t-test (* P≤0.05, **P≤0.01). "ns" represents no significant difference (P>0.05).

Figure 12:
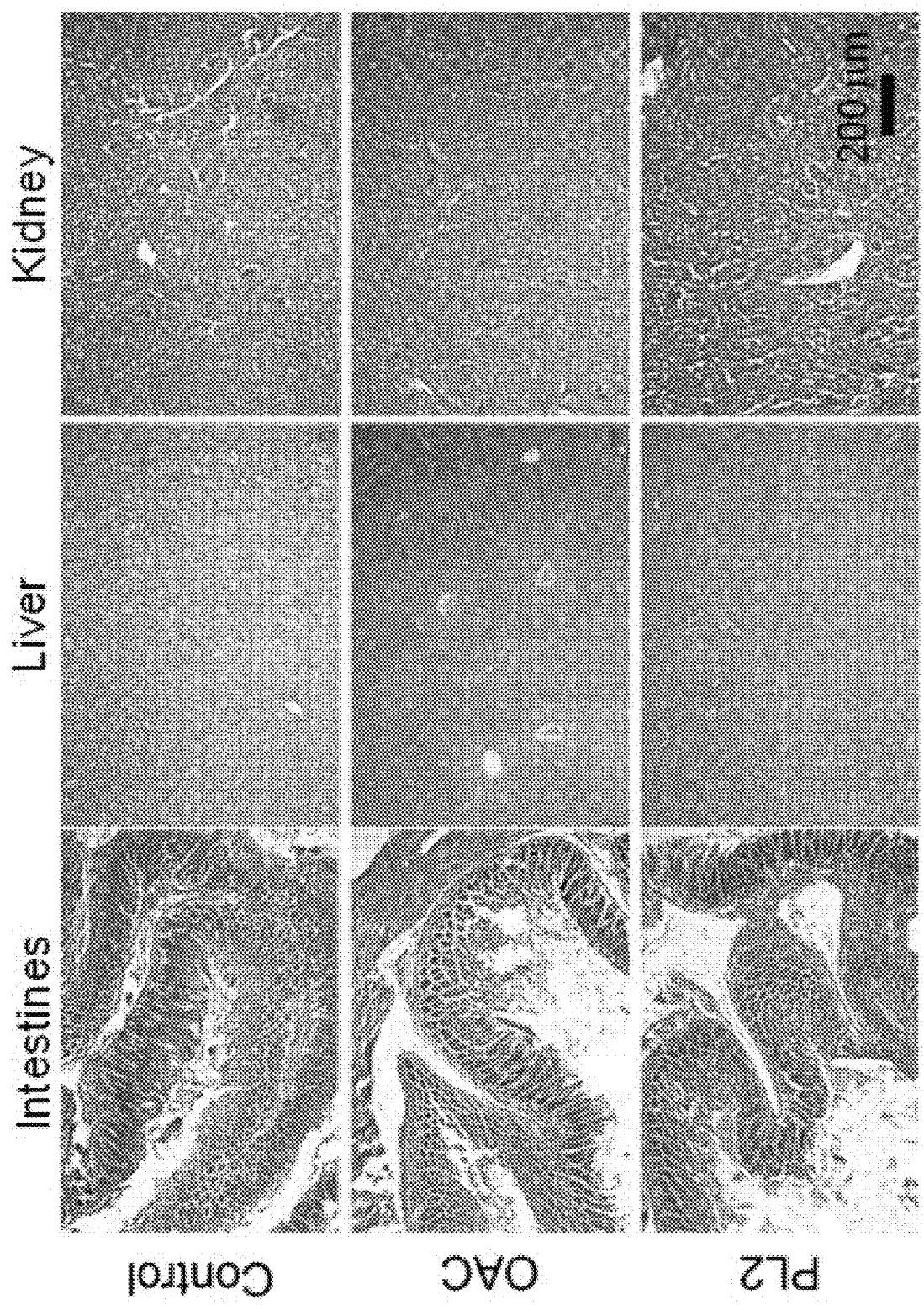

FIG. 12. The H&E-stained intestines, liver, and kidney from mice receiving control, OAC and PL2 (scale bar=200 μm).

DETAILED DESCRIPTION

Current clinical treatment of *Helicobacter pylori* infection, the main etiological factor in the development of gastritis, gastric ulcers, and gastric carcinoma, requires a combination of at least two antibiotics and one proton pump inhibitor. However, such triple therapy suffers from progressively decreased therapeutic efficacy due to the drug resistance and undesired killing of the commensal bacteria due to poor selectivity. Here, we report the development of antimicrobial polypeptide-based monotherapy, which can specifically kill *H. pylori* under acidic pH in the stomach while induce minimal toxicity to commensal bacteria under physiological pH. In one specific embodiment, we designed a class of pH-sensitive, helix-coil conformation transitionable antimicrobial polypeptides (HCT-AMPs) $(PGA)_m$-r-$(PHLG-MHH)_n$, bearing randomly distributed negatively-charged glutamic acid and positively-charged poly(γ-6-N-(methyldihexylammonium)hexyl-L-glutamate) (PHLG-MHH) residues. In other embodiments, related pH-sensitive, helix-coil conformation transitionable antimicrobial polypeptides of the formulas described herein are provided.

The HCT-AMPs showed unappreciable toxicity at physiological pH when they adopted random coiled conformation. Under acidic condition in the stomach, they transformed to the helical structure and exhibited potent antibacterial activity against *H. pylori*, including clinically isolated drug-resistant strains. After oral gavage, the HCT-AMPs afforded comparable *H. pylori* killing efficacy to the triple therapy approach while induced minimal toxicity against normal tissues and commensal bacteria, in comparison to the remarkable killing of commensal bacteria by 65% and 86% in the ileal contents and feces, respectively, following triple therapy. This strategy renders an effective approach to specifically target and kill *H. pylori* in the stomach while not harming the commensal bacteria/normal tissues.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The term "about" can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "alkyl" refers to a straight- or branched-chain alkyl group having from 1 to about 20 carbon atoms in the chain. For example, the alkyl group can be a $(C_1-C_{20})$alkyl, a $(C_1-C_{12})$alkyl, $(C_1-C_8)$alkyl, $(C_1-C_6)$alkyl, or $(C_1-C_4)$alkyl. Examples of alkyl groups include methyl (Me), ethyl (Et), i-propyl, isopropyl, butyl, isobutyl, sec-butyl, tert-butyl (t-Bu), pentyl, isopentyl, tert-pentyl, hexyl, isohexyl, and groups that in light of the ordinary skill in the art and the teachings provided herein would be considered equivalent to any one of the foregoing examples. Alkyl groups can be optionally substituted or unsubstituted, and optionally partially unsaturated, such as in an alkenyl group.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, pinenyl, and the like. The cycloalkyl group can be monovalent or divalent, and can be optionally substituted, for example, by one or more alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms.

Examples of heteroaryl groups include, but are not limited to, 2H-pyrrolyl, 3H-indolyl, 4H-quinolizinyl, acridinyl, benzo[b]thienyl, benzothiazolyl, O-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The heteroaryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and R are independently H, alkyl, alkenyl, aryl, heteroaryl, heterocycle, cycloalkyl, or hydroxy. For example, the nitrogen of any indolyl ring can be N-substituted to provide an N-alkyl, N-methyl, or N-protecting group indolyl compound. A heteroaryl can also be substituted with a substituent as described in the substituents definition below.

The term "heterocycle" or "heterocyclyl" refers to a saturated or partially unsaturated ring system, containing at least one heteroatom selected from the group oxygen, nitrogen, and sulfur, and optionally substituted with alkyl, or $C(=O)OR^b$, wherein $R^b$ is hydrogen or alkyl. Typically, heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine. The heterocycle can optionally be a divalent radical, thereby providing a heterocyclene.

The heterocycle can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy. A heterocycle can also be substituted with a substituent as described in the substituents definition below.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Protecting Groups. Compounds of the invention can further include one or more suitable protecting groups. The term "protecting group" refers to any group that, when bound to an sp-center, a hydroxyl, nitrogen, or other heteroatom prevents undesired reactions from occurring at this group and that can be removed by conventional chemical or enzymatic steps to reestablish the 'unprotected' moiety, such as an alkyne, hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidine, phenacyl, methyl methoxy, silicon protecting groups ("silyl ethers") (e.g., trimethylsilyl (TMS), t-butyl-diphenylsilyl (TBDPS), triisopropylsilyl (TIPS), or t-butyldimethylsilyl (TBS)) and any other group that can be introduced chemically onto a hydroxyl or other moiety and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Greene describes many nitrogen-protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (Georg Thieme Verlag Stuttgart, N.Y., 1994), which is incorporated herein by reference in its entirety. Some specific protecting groups that can be employed in conjunction with the methods of the invention are discussed below.

The term "halogen" refers to chlorine, fluorine, bromine or iodine. The term "halo" refers to chloro, fluoro, bromo or iodo.

As to any of the groups or "substituents" described herein (e.g., groups $R^1$, $R^2$, and $R^3$), each can further include one or more (e.g., 1, 2, 3, 4, 5, or 6) substituents. It is understood, of course, that such groups do not contain any substitution or substitution patterns which are sterically impractical and/or synthetically non-feasible.

The term "substituted" means that a specified group or moiety can bear one or more (e.g., 1, 2, 3, 4, 5, or 6) substituents. The term "unsubstituted" means that the specified group bears no substituents. The term "optionally substituted" means that the specified group is unsubstituted or substituted by one or more substituents, and elements of the Formulas described herein can be optionally substituted. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted in some embodiments but can be substituted in other embodiments. In other words, the variables $R^1$, $R^2$, and $R^3$ and their elements can be optionally substituted. In various embodiments, suitable substituent groups (e.g., on groups $R^1$, $R^2$, and $R^3$ and/or their elements) include one or more of alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and/or cyano. Additionally, suitable substituent groups can be, e.g., —X, —R, —OH, —OR, —SR, —S—, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, C(=O)NRR, —S(=O)$_2$H, —S(=O)$_2$OH, —S(=O)$_2$R, —OS(=O)$_2$OR, —S(=O)$_2$NHR, —S(=O)R, —C(=O)R, —C(=O)X, —C(S)R, —C(O)OR, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In certain embodiments, any one of the above groups can be included or excluded from a variable (e.g., groups $R^2$ and $R^3$) or from a group of substituents.

The pharmaceutically acceptable salts of the compounds described herein can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of many suitable salts are found in *Remington: The Science and Practice of Pharmacy*, 21$^{st}$ edition, Lippincott, Williams & Wilkins, (2005).

The term "solvate" refers to a solid compound that has one or more solvent molecules associated with its solid structure. Solvates can form when a solid compound is crystallized from a solvent, wherein one or more solvent molecules become an integral part of the solid crystalline matrix. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

The term "diluent" refers to a pharmacologically inert substance that is nevertheless suitable for human consumption that serves as an excipient in the inventive dosage form. A diluent serves to dilute the API in the inventive dosage form, such that tablets of a typical size can be prepared incorporating a wide range of actual doses of the API.

The term "excipient" refers to an ingredient of the dosage form that is not medicinally active, but serves to dilute the API, assist in dispersion of the tablet in the patient's stomach, bind the tablet together, and serve other functions like stabilizing the API against decomposition.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. An appropriate "effective" amount in any individual case may be determined using techniques, such as a dose escalation study.

The terms "treating", "treat" and "treatment" include (i) inhibiting the disease, pathologic or medical condition or arresting its development; (ii) relieving the disease, pathologic or medical condition; and/or (iii) diminishing symptoms associated with the disease, pathologic or medical condition. Thus, the terms "treat", "treatment", and "treating" can include lowering, stopping or reversing the progression or severity of the condition or symptoms being treated. As such, the term "treatment" can include medical and/or therapeutic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

Under acidic conditions, such as in the stomach of most mammals, the polypeptide forms a helical structure and has membrane activity, capable of killing bacteria. By "acidic pH," it is meant a pH of about 1 to a pH of about 5. Under physiological pH, the polypeptide does not form a helical structure and has diminished or lacking membrane activity, and is not capable of effectively killing bacteria. By "physiologic p," it is meant a pH of about 5 to a pH of about 8.

Selective Killing of *Helicobacter pylori* with pH-Responsive Helix-Coil Conformation Transitionable Antimicrobial Polypeptides In this disclosure, we describe the design of a class of pH-responsive HCT-AMPs as a single bactericidal agent that can specifically target *H. pylori* under the acid condition in the stomach. Random polypeptide copolymers $(PGA)_m$-r-$(PHLG\text{-}MHH)_n$ were developed with randomly distributed negatively-charged Glu residues and positively-charged PHLG-MHH residues. The conformation and membrane activity of the polypeptides depend on the charge state of Glu residues. At physiological pH, the polypeptides adopt random coiled conformation with low toxicity, while in the stomach under acidic condition, they are converted to the helical conformation with potent membrane disruption capability to effectively kill *H. pylori*. With such design, HCT-AMPs showed minimal toxicity against normal tissues/commensal bacteria but in vivo *H. pylori* killing efficacy comparable to the triple therapy, with remarkably improved selectivity for anti-*H. pylori* therapy.

Figure 5:
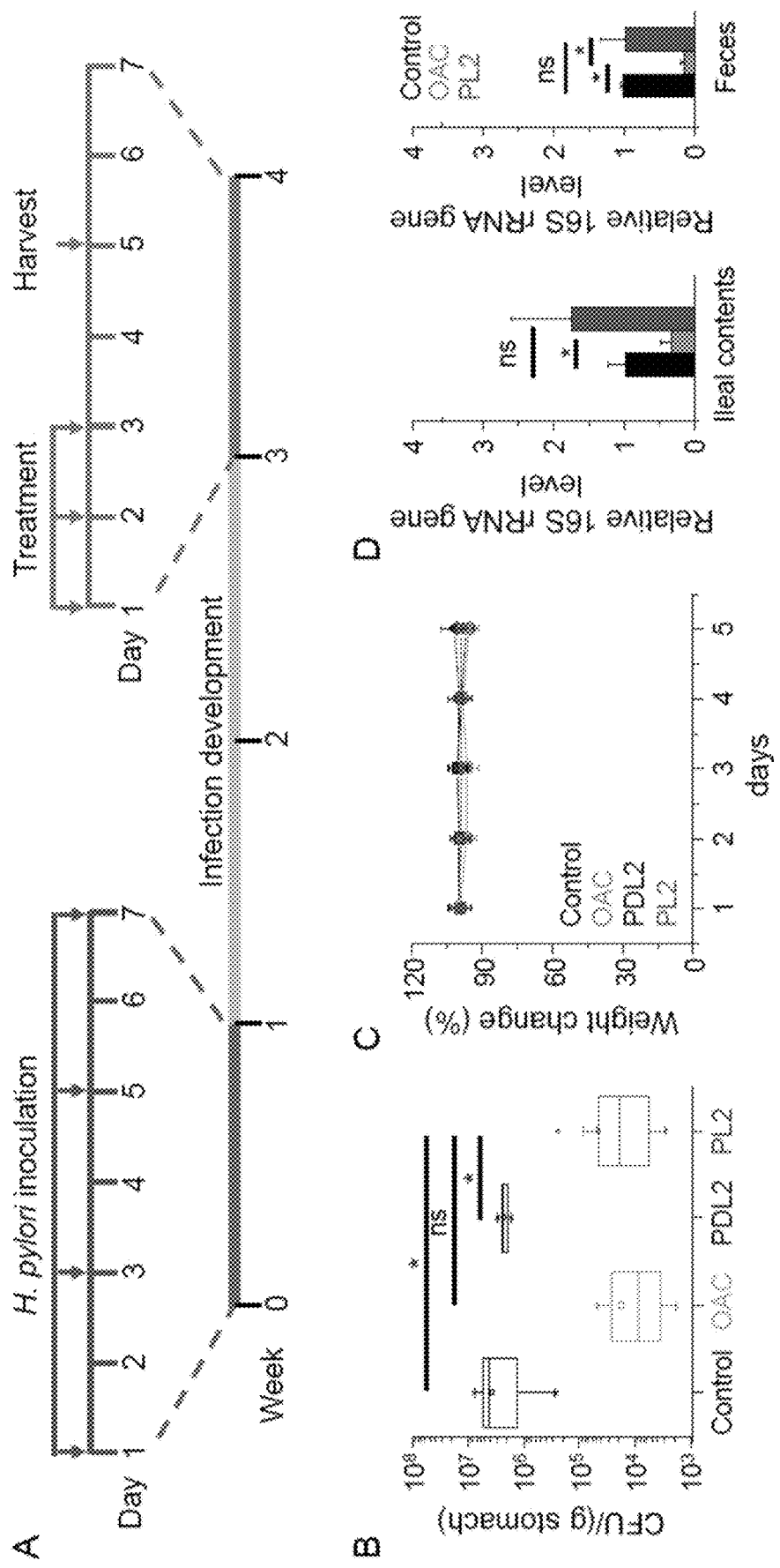
FIG. 5. Anti-*H. pylori* efficacy of HCT-AMPs in vivo. (A) The study protocol of *H. pylori* inoculation, infection development and treatments in C57BL/6J mice. Each mouse were administered with SS1 ($OD_{600}$=2, 0.2 mL) intragastrically through oral gavage every other day for four times (on days 1, 3, 5 and 7, respectively), and the infection was allowed to develop for 2 weeks. Mice were then treated with control (PBS), triple therapy (OAC, omeprazole 400 µmol/kg, amoxicillin 68 µmol/kg, and clarithromycin 19.1 µmol/kg), PDL2 and PL2 (2.6 µmol/kg) once daily for a consecutive 3 d. (B) Bacterial burden in the stomach of *H. pylori*-infected mice treated with PBS, triple control therapy, PDL2, and PL2 (n 6). (C) Body weight change of mice following treatment of various formulations as in (B). (D) The killing effect of PL2 against commensal bacteria determined by measuring the bacterial load in the feces and ileal contents of mice after a daily gavage of PL2, Control (5% DMSO) and OAC for 3 consecutive days. The bacterial load was determined by quantitative real-time PCR. The 16S rRNA gene level was normalized to the tissue weight (n≥6). All of the data are represented as average±SD and analyzed by student's t-test (* P≤0.05). "ns" represents no significant difference (P>0.05).

Commensal bacteria have gained increased attention due to their important functions during the physiological and metabolic processes as well as the development of the immune system. Undesired alteration of the microbiome can disturb the symbiotic relationship between resident microorganisms and the digestive tract, and thus induce the occurrence as well as progression of various diseases, including but not limited to inflammatory bowel disease, colon cancer, Parkinson's disease, obesity, diabetes, atherosclerosis, and allergy. Recent research has also shown that the elimination of commensal bacteria significantly alleviates the efficacy of anti-cancer therapeutics, including CTLA-4 and PD-LI blockade-mediated cancer immunotherapy. Therefore, development of therapeutics that can selectively kill *H. pylori* without harming commensal bacteria is highly attractive and important. The triple therapy, used in clinical *H. pylori* treatment, killed 65% and 86% of the commensal bacteria in the ileal contents and feces, respectively, while the pH-sensitive HCT-AMPs showed unappreciable toxicity against commensal bacteria (FIG. 5D). This strategy therefore represents an ideal and promising approach to target and selectively kill *H. pylori* in the stomach without provoking damage to commensal bacteria.

Figure 2:
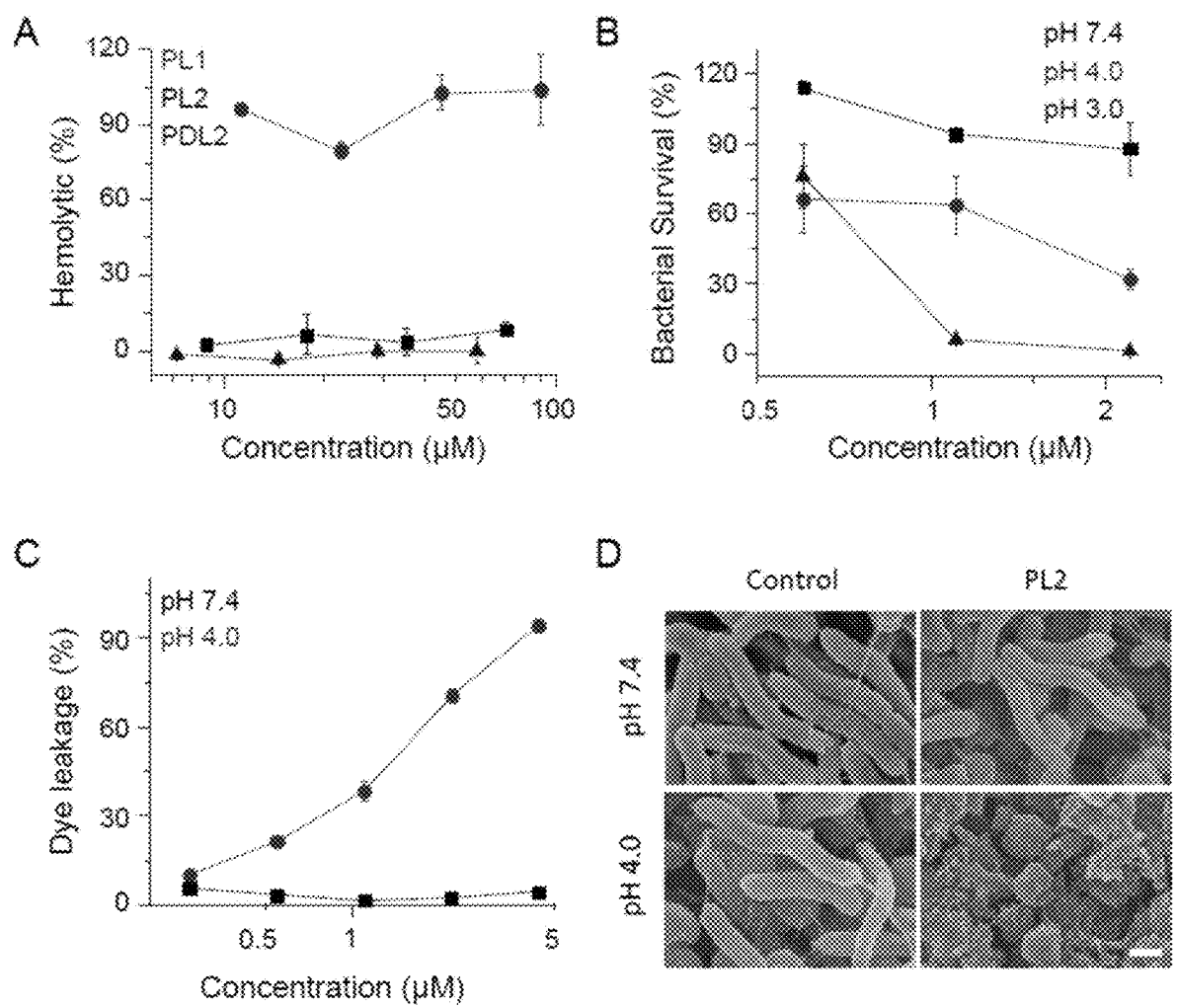
FIG. 2. HCT-AMPs selectively kill *H. pylori* under acidic condition in vitro. (A) The hemolytic activity of polypeptides at pH 7.4. PL1, PL2 and PDL2, dissolved in PBS (pH 7.4) at various concentrations, were incubated with fresh rabbit blood for 1 h. Hemoglobin release was measured by UV-absorbance at 576 nm using a microplate reader. (B) The survival rate of *H. pylori* SS1 after incubation with PL2 for 1 h at various pHs. PL2, dissolved in the Tris-HCl buffer at various pHs (pH 7.4, 4.0, 3.0), was incubated with SS1 at corresponding pHs in *brucella* broth (BB) medium supplied with fresh urea (10 mM), 10% fetal bovine serum (FBS) and vancomycin (5 µg/mL). The bacterial count was determined by counting column forming unites (CFU) of alive bacteria with agar plating. Bacteria incubated with Tris-HCl buffer only at corresponding pH were served as 100% survival. (C) Extent of ANTS/DPX efflux in negatively charged liposomes after treatment with PL2 at various concentrations at pH 7.4 or pH 4.0. (D) SEM images of SS1 after treatment with Tris-HCl buffer or PL2 at pH 7.4 or pH 4.0. SS1 bacterial cells were incubated with or without PL2 (2.2 µM) at pH 7.4 or 4.0 for 30 min. Bar=0.5 µm.
Figure 3:
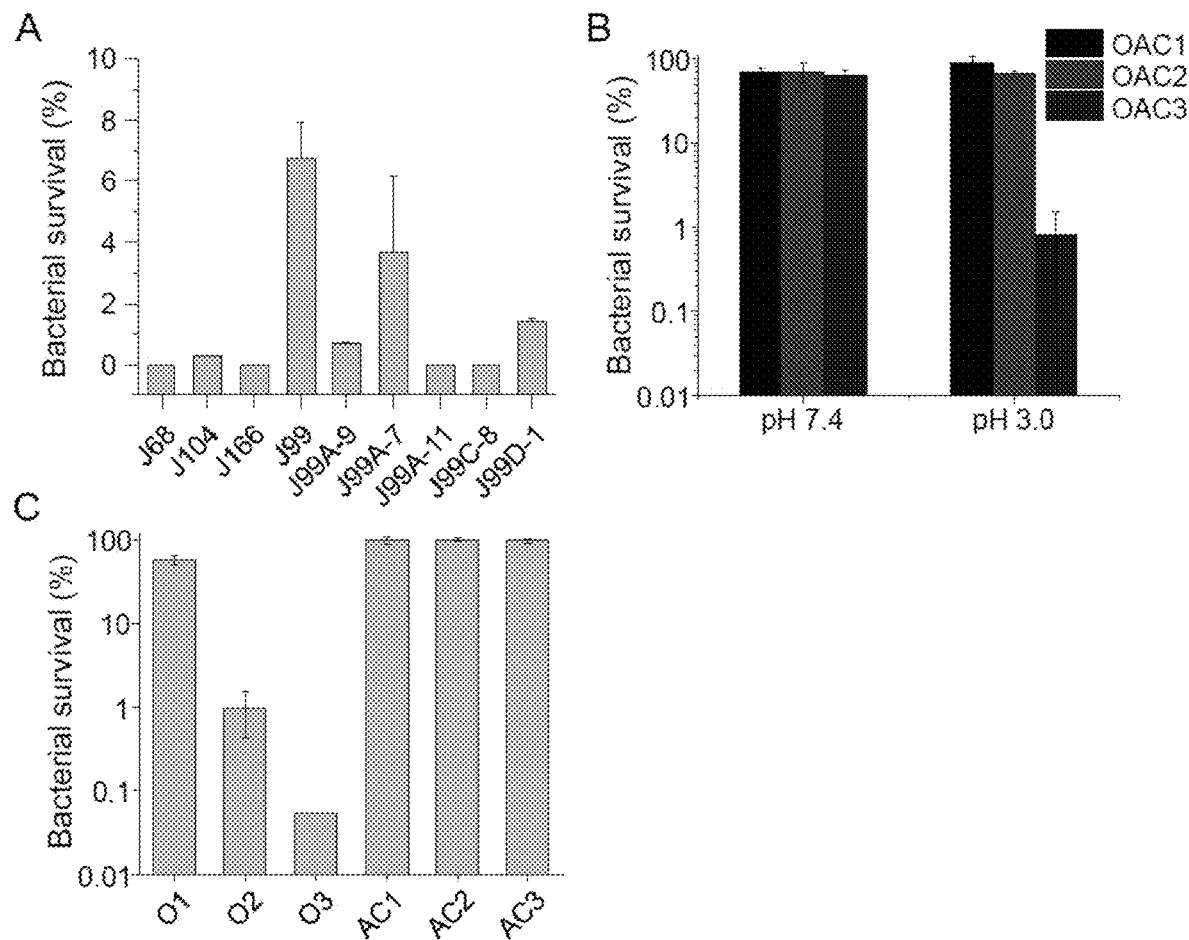
FIG. 3. HCT-AMPs effectively kill clinically isolated drug resistant *H. pylori*. (A) The bactericidal activity of PL2 against clinically isolated *H. pylori* strains. PL2, dissolved in the Tris-HCl buffer (pH 3.0), were incubated with clinically isolated strains in BB medium supplied with fresh urea, FBS and vancomycin (pH 3.0) for 1 h. The final concentration of PL2 was 4.4 µM. (B) The antibacterial activity of triple therapy against J99A-11 at pH 7.4 or 3.0. Concentrations of omeprazole, amoxicillin, and clarithromycin in OAC1 are 20.0 µM, 6.8 µM, and 1.9 µM, respectively; in OAC2 are 40.0 µM, 13.6 µM, and 3.8 µM, respectively; in OAC3 are 80.0 µM, 27.2 µM, and 7.6 µM, respectively (bars, left to right). (C) The antibacterial activity of omeprazole (O) and a combination of amoxicillin and clarithromycin (AC) against J99A-11 at pH 3.0. O1, O2, O3 represents the concentration of omeprazole at 20.0 µM, 40.0 µM, and 80.0 µM, respectively. AC1, AC2, AC3 represents the concentration of amoxicillin and clarithromycin at 6.8 µM and 1.9 µM, 13.6 µM and 3.8 µM, 27.2 µM and 7.6 µM, respectively.

Apart from the undesired toxicity, the triple therapy also suffers from the progressive increase of drug resistance that undermines its therapeutic efficacy against *H. pylori*-induced gastric diseases. High resistance rates are noted for clinically used antibiotics, such as 60-70% for metronidazole, 20-38% for clarithromycin, and 30-38% for levofloxacin (Zhang et al. (2015) *World J Gastroenterol* 21:13432-13437). In the current study, HCT-AMPs kill bacteria mainly by disrupting the membrane integrity (FIG. 2D), a highly destructive mechanism for bacterial killing with low susceptibility for resistance development. As such, we demonstrated that HCT-AMPs could effectively kill clinically isolated drug-resistant bacterial strains (FIG. 3A). The clinical success of triple therapy is also greatly hurdled by the resistance to PPI, because in many patients, PPI cannot effectively increase their gastric pH, thus leading to low antimicrobial activity of antibiotics in the gastric fluid. The HCT-AMPs developed herein kill *H. pylori* under acidic condition as a single agent, and they exhibited increased anti-*H. pylori* efficacy with the decrease of pH (FIG. 2B), effectively bypassing the problem of PPI resistance. Based on these results, it is expected that the HCT-AMPs would outperform the classical triple therapy during anti-*H. pylori* therapy.

PL2 (Scheme 1 and FIG. 1A) was synthesized via the reaction of PCHLG$_{20}$-r-PtBLG$_{18}$ with N-methyldihexylamine followed by removal of the tert-butyl group by trifluoracetic acid. Details describing preparation and characterization of HCT-AMPs, in vitro and in vivo antibacterial assays, and hemolytic assay are found in the Examples below.

HCT-AMPs display pH-sensitive helix-coil transition. Random copolypeptides PL2, (PGA)$_{18}$-r-(PHLG-MHH)$_{20}$, with anionic glutamic acid (Glu) and cationic poly(γ-6-N-(methyldihexylammonium)hexyl-L-glutamate) (PHLG-MHH) residues (FIG. 1A) were developed via the ring-opening polymerization of L-γ-(6-chlorohexyl)-Glu-based N-carboxyanhydrides (NCA) and L-tert-butyl-Glu-NCA (tBLG-NCA) (i), followed by amination (ii) and trifluoroacetic acid-assisted de-esterification (iii) (Scheme 1, Example 1) (Xiong et al. (2015)*Proc Natl Acad Sci USA* 112:13155-13160; Lu and Cheng (2007) *J Am Chem Soc* 129:14114-14115).

Scheme 1. Synthetic route of antimicrobial polypeptides PL2, PL1 and PDL2

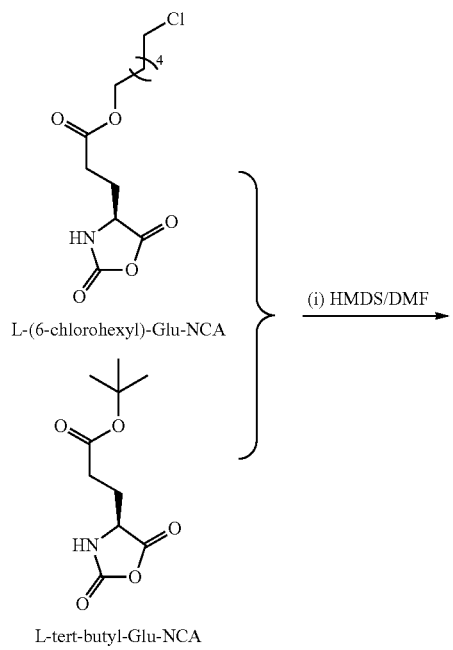

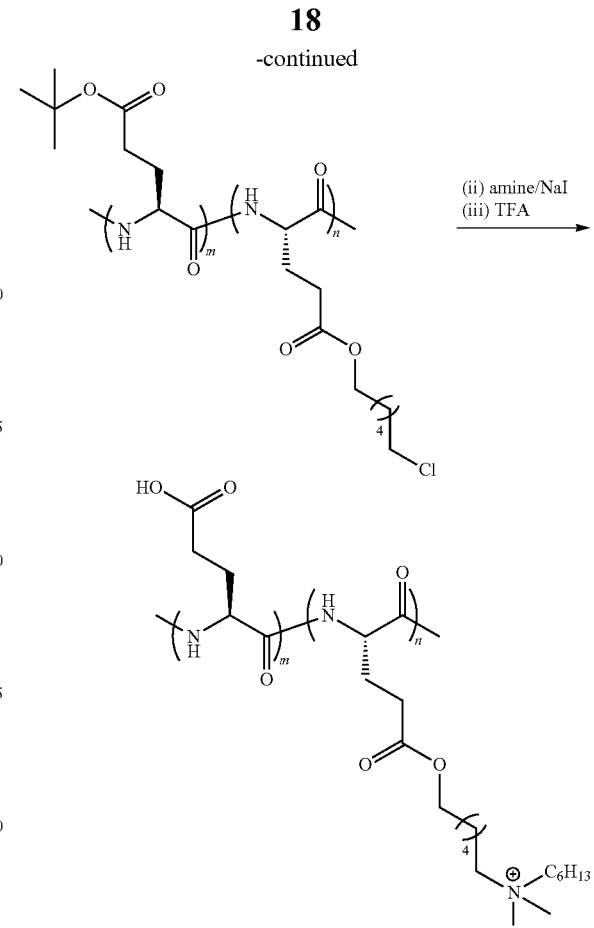

(PGA)$_m$-r-(PHLG—MHH)$_n$ Structure
PL1: (PHLG—MHH)$_{20}$
PL2: (PGA)$_{18}$-r-(PHLG—MHH)$_{20}$
PDL2: (PDLGA)$_{20}$-r-(PHDLG—MHH)$_{25}$ pH-independent helical polypeptide and nonhelical polypeptides (prepared with D,L-γ-(6-chlorohexyl)-Glu-NCA) and DL-tert-butyl-Glu-NCA as monomers) were synthesized as control polypeptides, named as PL1=(PHLG-MHH)$_{20}$, PDL2=(PDLGA)$_{20}$-r-(PHDLG-MHH)$_{25}$ (Scheme 1, Table 1, Example 1). The structure of the polypeptides was confirmed by $^1$H-NMR spectra.

TABLE 1

The characterization of random polypeptides PCHLG$_{20}$-r-PtBLG$_{18}$ and PCHDLG$_{25}$-r-PtBDLG$_{20}$.

| Polypeptide | $M_n$ (kDa) | $M_w/M_n$ |
|---|---|---|
| PCHLG$_{20}$-r-PtBLG$_{18}$ | 9.4 | 1.10 |
| PCHDLG$_{25}$-r-PtBDLG$_{20}$ | 12.7 | 1.28 |

Figure 1:
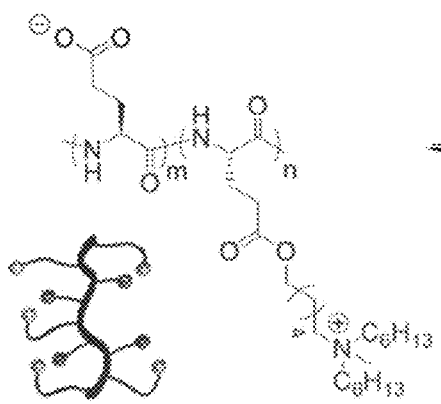
FIG. 1. HCT-AMPs display pH-sensitive helix-coil transition. (A) Schematic illustration of the pH-responsive conformation transition of HCT-AMP (PGA)$_{18}$-r-(PHLG-MHH)$_{20}$ ("PL2", a random polymer polypeptide). It adopts random coiled conformation at physiological pH to impart low toxicity while transforms to helical conformation under acidic condition in the stomach to induce potent antimicrobial activity against *H. pylori*. The green "+" balls represent cationic amine groups, the blue "—" balls represent anionic group (—$COO^-$) and the black (solid) balls represent neutral groups (—COOH). CD spectra of PL2 (4.4 µM) at various pH values adjusted from 7.4 to 2.7 with 1 M HCl (B) and from 2.7 to 7.2 with 1 M NaOH.
Figure 1:
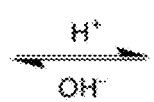
Figure 1:
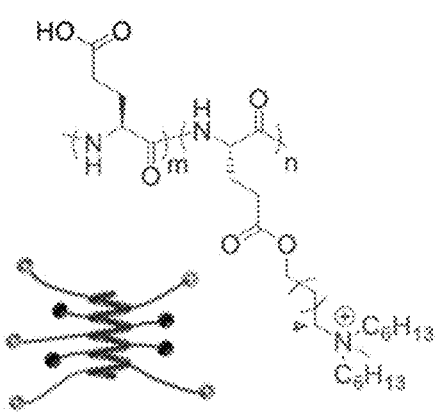
Figure 1:
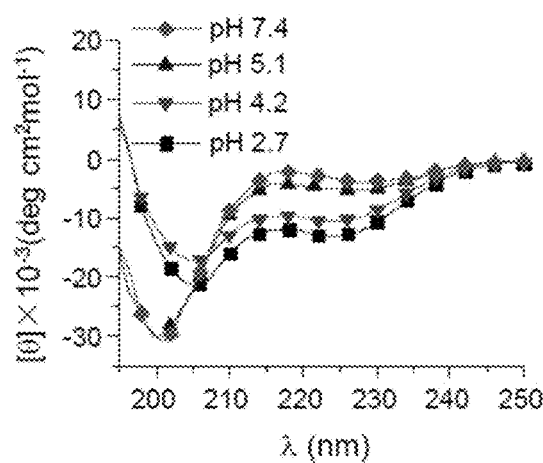
Figure 1:
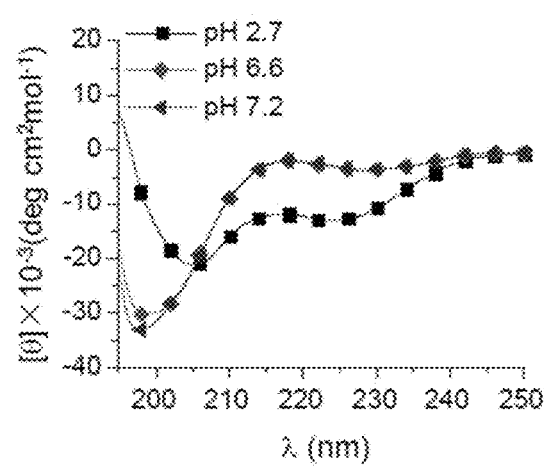
Figure 6:
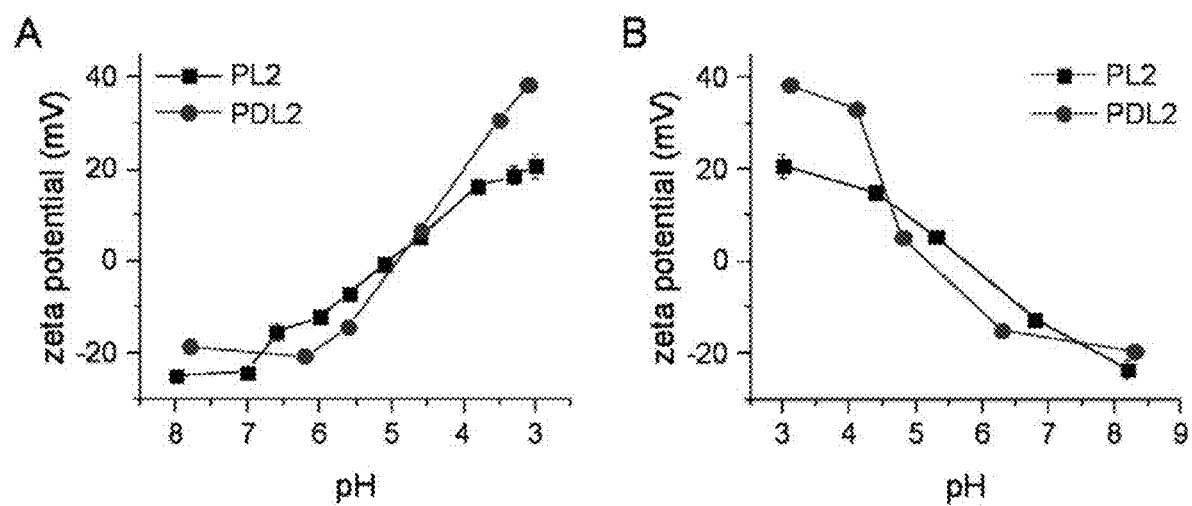
FIG. 6. The zeta potential of PL2 and PDL2 at different pH value adjusted from 8.0 to 3.0 (by 0.1 M HCl, A) and from 3.0 to 8.0 (by 0.1 M NaOH, B).
Figure 7:
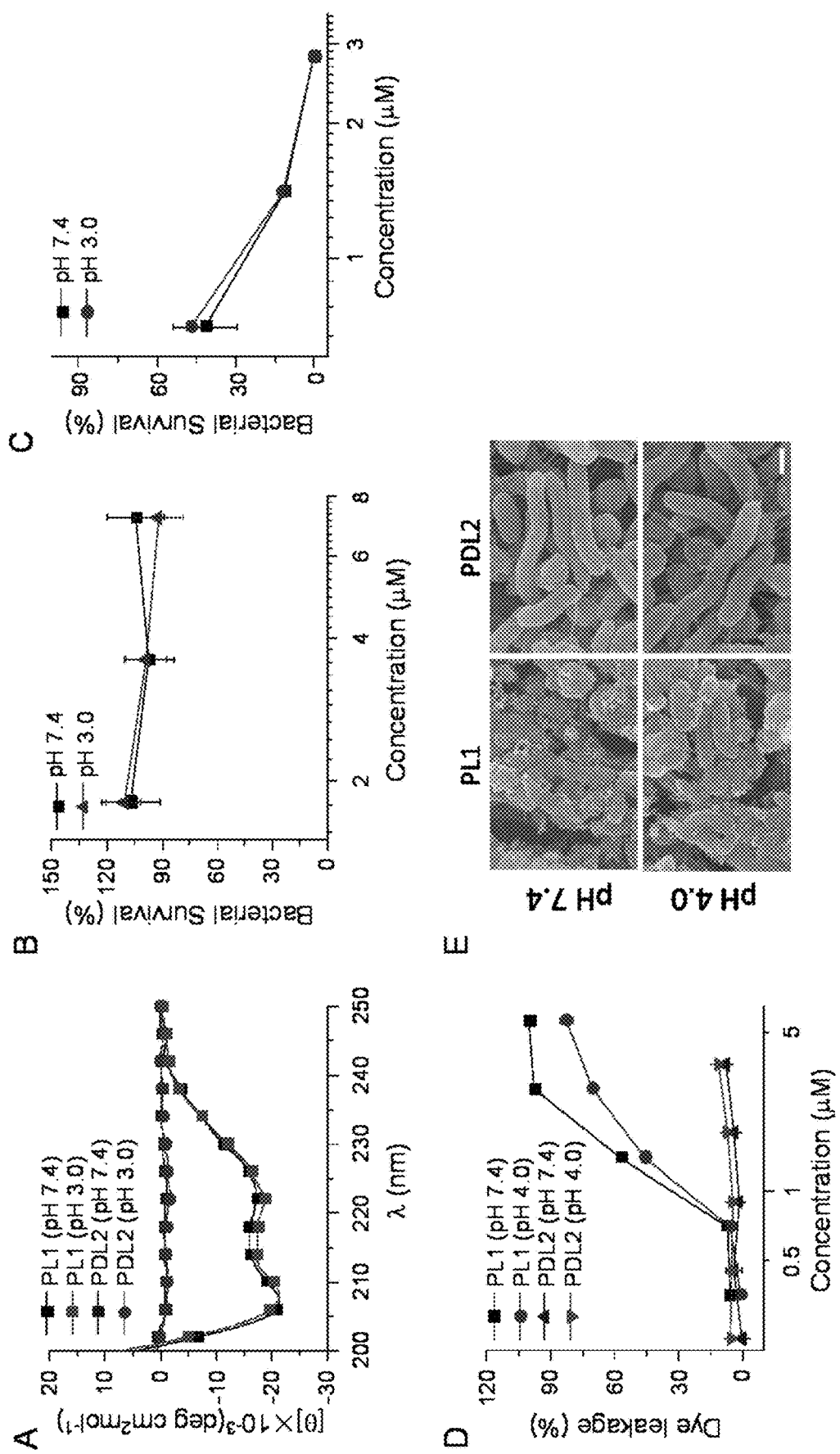
FIG. 7. (A) CD spectra of PL1 and PDL2 under pH 7.4 or 3.0. The survival rate of *H. pylori* SS1 after incubation with PDL2 (B) and PL1 (C) under pH 7.4 or 3.0 for 1 h. (D) Extent of ANTS/DPX efflux in negatively charged liposome after treatment with PL1 and PDL2 at various concentrations under pH 7.4 or pH 4.0. (E) SEM images of SS1 after treatment with PL1 or PDL2 at pH 7.4 or pH 4.0. SS1 bacterial cells were incubated with or without polypeptides (2.2 µM) for 30 min under pH 7.4 or 4.0. Bar=0.5 sm.

The secondary structure of the polypeptides at different pH value was then investigated by circular dichroism (CD). As shown in FIG. 1B, the secondary structure of PL2 was related to the charge status of PGA (pKa~4.5) (FIG. 6 and Example 2). Particularly, at pH≥5.1 when the carboxyl groups exhibited negative charge, PL2 adopted random coiled conformation due to the intermolecular electrostatic interaction between the negatively charged carboxyl groups and the positively charged amine groups of PHLG-MHH. In contrast, at pH≤4.2 when the carboxyl groups were protonated, PL2 restored typical helical conformation as evidenced by the double minima at 208 nm and 222 nm, which was attributed to the depletion of side-chain charge interactions. Distortion of helical conformation was noted when the pH was adjusted back to neutral (FIG. 1C). In consistence with such findings, PL1 containing only the cationic PHLG-MHH segment displayed stable helical conformation independent of pH change (FIG. 7A). PDL2, a racemic analogue of PL2, also demonstrated pH-independent non-helical conformation.

HCT-AMPs selectively kill *H. pylori* in vitro. With respect to its pH-responsive secondary structure, the HCT-AMP is expected to show low toxicity at neutral pH while high antibacterial activity against *H. pylori* in the acidic gastric environment. To test this hypothesis, we first evaluated the hemolytic activity of the polypeptides at pH 7.4. PL2 and PDL2, affording random coiled structure at pH 7.4, showed no hemolytic activity at a high concentration up to 70 μM, while PL1 with stable helical structure caused remarkable hemolysis at 10 μM, which further substantiated the helical conformation-dependent membrane toxicity against erythrocytes (FIG. 2A).

Additionally, PL2 showed low antibacterial activity against *E. coli* DH5α and MG1655 at pH 7.4, affording the minimal inhibitory concentration (MIC) higher than 70 μM. Such results indicate that PL2 would not kill commensal bacteria in the intestine with relatively neutral pH. We then determined the bactericidal activity of HCT-AMPs against *H. pylori* SS1 strain under various pH conditions. Upon incubation of SS1 with PL2 at pH 7.4 for 1 h, no bactericidal activity was noted. However, notable bacteria killing was achieved by PL2 at pH 4.0, and further decreased pH value correlated to higher bactericidal activity (FIG. 2B). As a comparison, the non-helical PDL2 exhibited unappreciable bactericidal activity at both pH 7.4 and 3.0 and the helical PL1 killed *H. pylori* SS1 at both pH levels (FIG. 7B and FIG. 7C; Example 2). These results collectively indicate that the restoration of helical structure is essential for PL2 to selectively kill *H. pylori* under the gastric acidic condition, and the loss of helical conformation under intestinal neutral condition may contribute to the low toxicity against commensal bacteria.

Figure 8:
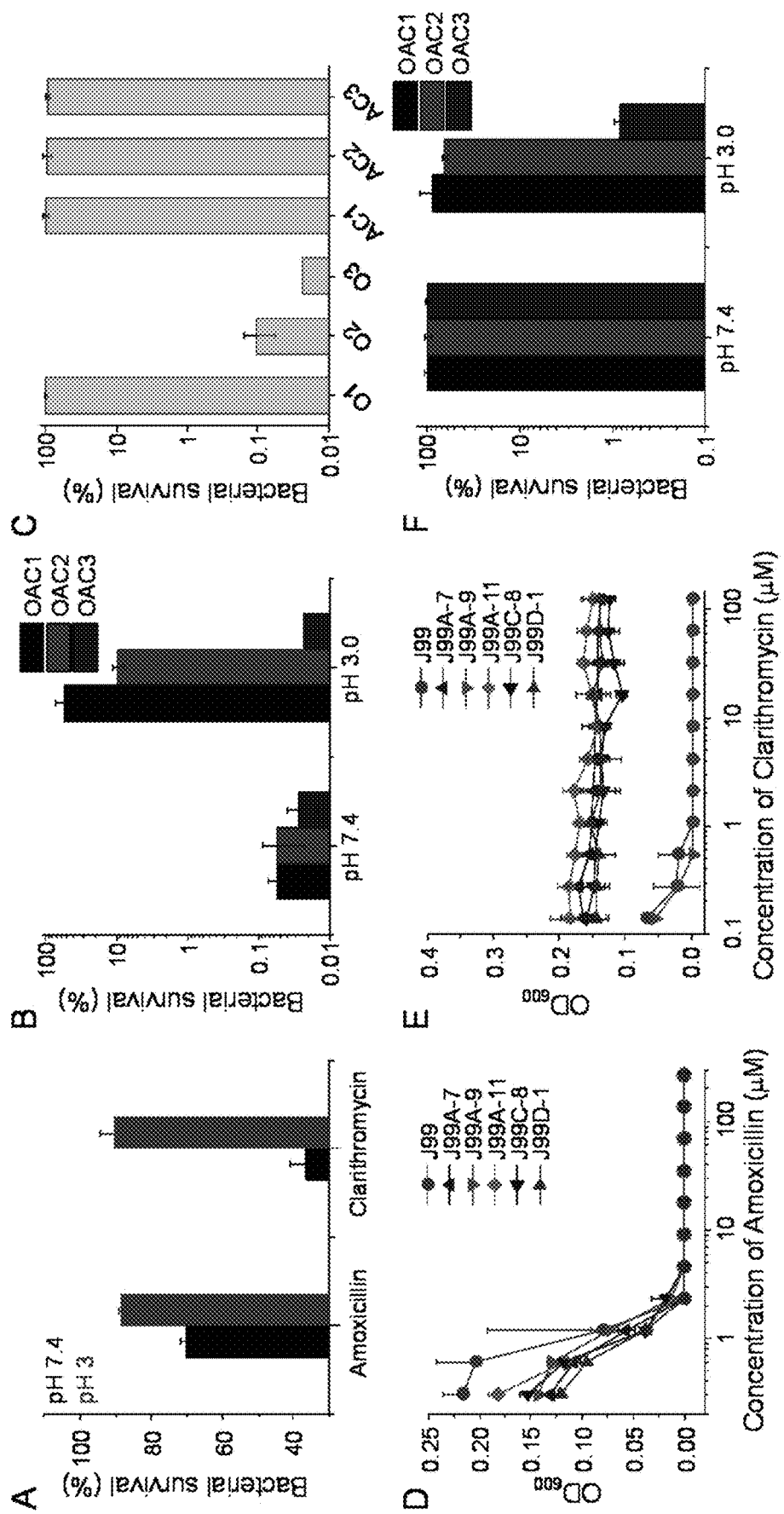
FIG. 8. (A) The survival rate of *H. pylori* after incubation with amoxicillin (273.7 µM) and clarithromycin (133.7 µM) under pH 7.4 or 3.0 for 1 h. (B) The antibacterial activity of triple therapy OAC (a combination of omeprazole, amoxicillin and clarithromycin) against SS1 under pH 7.4 or 3.0. Concentrations of omeprazole, amoxicillin, and clarithromycin in OAC1 are 20.0 µM, 6.8 µM, and 1.9 µM, respectively; in OAC2 are 40.0 µM, 13.6 µM, and 3.8 µM, respectively; in OAC3 are 80.0 µM, 27.2 µM, and 7.6 µM, respectively. (C) The antibacterial activity of omeprazole (O) and a combination of amoxicillin and clarithromycin (AC) against SS1 at pH 3.0. O1, O2, O3 represents the concentration of omeprazole at 20.0 µM, 40.0 µM, and 80.0 µM, respectively. AC1, AC2, AC3 represents the concentration of amoxicillin and clarithromycin at 6.8 µM and 1.9 µM, 13.6 µM and 3.8 µM, 27.2 µM and 7.6 µM, respectively. The antibiotics were incubated with *H. pylori* strains for 1 h. The antibacterial activity of amoxicillin (D) and clarithromycin (E) against clinical isolated *H. pylori* stains, J99, J99A-7, J99A-9, J99A-11, J99C-8, J99D-1. The bacteria were incubated with antibiotics under pH 7.4 in the 10% $CO_2$ incubator (37° C.), and the optical density at 600 nm ($OD_{600}$) of bacteria were analyzed to determine the growth of bacteria. The result indicated that J99A-7, J99A-11, J99C-8 and J99D-1 are resistant to clarithromycin. (F) The antibacterial activity of OAC against J99D-1 under pH 7.4 or 3.0. (G) The antibacterial activity of omeprazole (0) and a combination of amoxicillin and clarithromycin (AC) against J99D-1 under pH 3.0.
Figure 8:
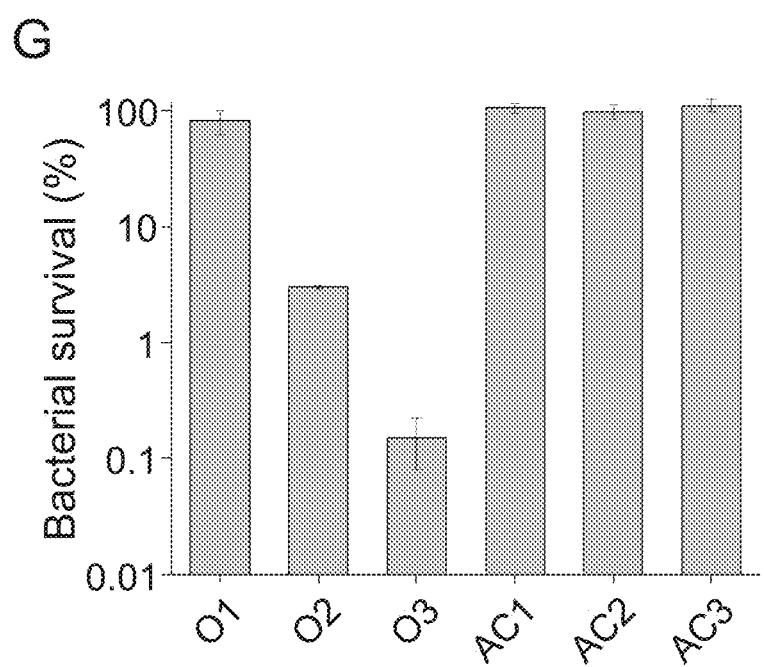

A combination of omeprazole, amoxicillin and clarithromycin (OAC) are used for the treatment of *H. pylori* infection in clinic. We further explored the bactericidal activity of these antibiotics under the same condition to allow direct comparison with PL2. Although the MIC of amoxicillin and clarithromycin against SS1 was as low as 0.13 μM and 0.07 μM, respectively, amoxicillin and clarithromycin only killed ~40% and ~60% of the bacteria at pH 7.4 after 1 h incubation at high concentrations of 273.7 μM and 133.7 μM, respectively, indicating the slow function of antibiotics (FIG. 8A; Example 2). Moreover, these two antibiotics showed no bactericidal activity against SS1 at pH 3.0, rationalizing why PPI is demanded to raise the pH of the stomach to potentiate the antibiotic-mediated treatment of *H. pylori* infection in vivo. A combination of OAC effectively killed SS1 in 1 h at both pH 7.4 and 3.0 (FIG. 8B). The antibacterial activity of OAC at pH 3.0 was attributed to the bacterial killing effect of omeprazole, while a combination of amoxicillin and clarithromycin (AC) showed no antibacterial activity at pH 3.0 (FIG. 8C). It should be noted that omeprazole performs differently in vitro and in vivo. Omeprazole is used for the increase of the gastric pH in order to enhance the antimicrobial activity and stability of antibiotics in the gastric fluid in vivo. It suppresses stomach acid secretion via specific inhibition of the $H^+/K^+$-ATPase system found at the secretory surface of gastric parietal cells. Because of the unique mechanism, omeprazole cannot increase the pH value of the acidic medium during the bacterial killing study in vitro. Instead, omeprazole readily converts to the active sulfenamide form and causes a substantial decrease in survival of *H. pylori* under acidic condition in vitro.

Figure 9:
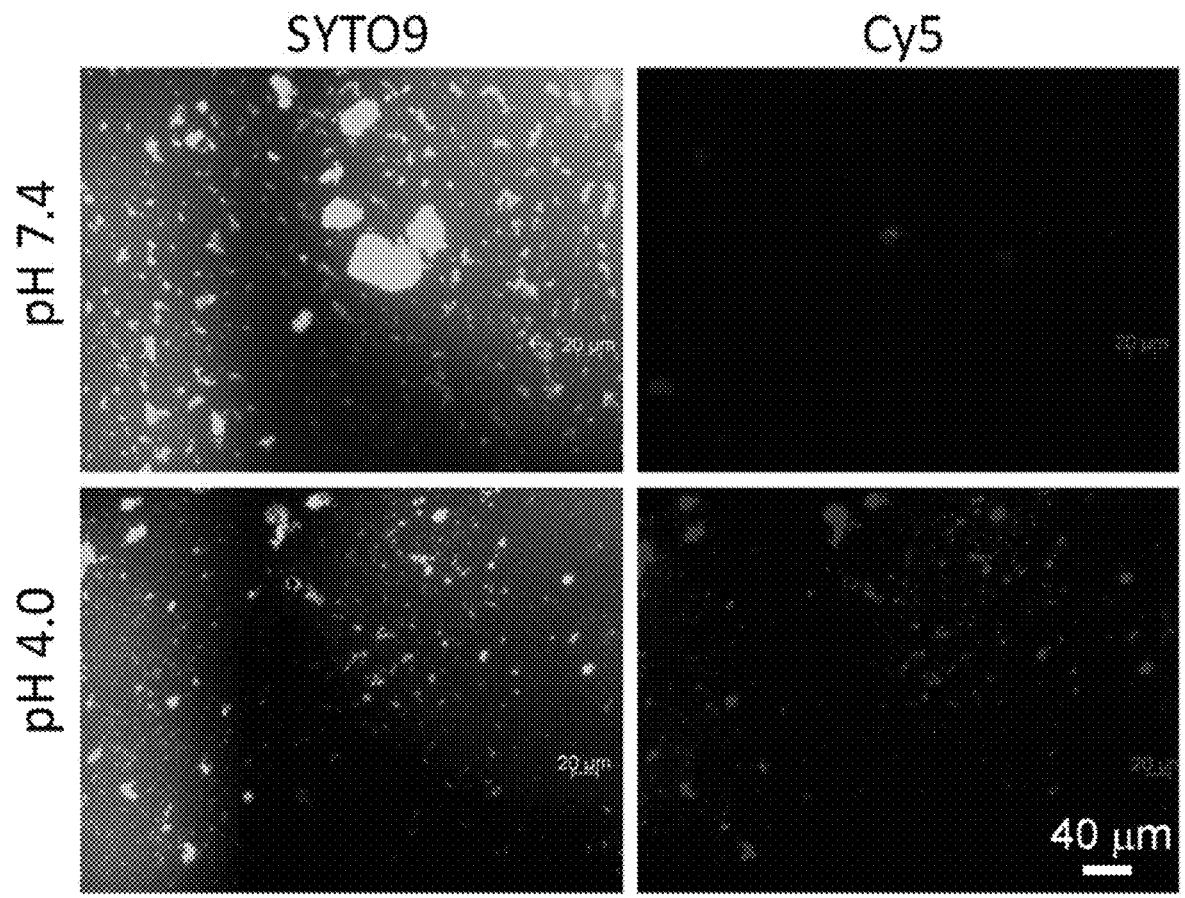
FIG. 9. Fluorescent imaging of *H. pylori* SS1 after incubation with Cy5-PL2 at pH 7.4 or 4.0 for 1 h. The green fluorescence represents SYTO9, which can stain the live bacteria; and the red fluorescence represents Cy5-labeling polypeptide. At pH 7.4, almost no Cy5 fluorescent signal was detected in the bacteria, while strong Cy5 fluorescent signal was detected in the bacteria under pH 4.0. The result indicated that more Cy5-PL2 bound to SS1 bacterial cells at pH 4.0 than at pH 7.4, which was attributed to the formation of catatonically helical structure at acidic pH that promoted binding of polypeptide molecules into phospholipid bilayers.

The bactericidal mechanism of HCT-AMPs was further explored by the vesicle leakage assessment as well as bacteria morphology observation. PL2 was labeled with Cy5 (Cy5-PL2), and its binding with bacteria membranes was observed using fluorescence microscopy. More Cy5-PL2 bound to SS1 bacterial cells at pH 4.0 than at pH 7.4 (FIG. 9; Example 2), which was attributed to the formation of cationcally helical structure at acidic pH that promoted binding of polypeptides to phospholipid bilayers. The membrane activity of the polypeptides was studied at both pH 7.4 and 4.0 by assessing dye leakage from anionic liposomes, a commonly used model to simulate the phosphatidylethanolamine-rich bacterial cell membrane. After incubation, PL2 induced great dye leakage from the liposome at pH 4.0 while inducing minimal dye leakage at pH 7.4 (FIG. 2C).

These results demonstrate that the acid-triggered helix formation of HCT-AMPs allows them to directly disrupt the bacteria membranes, a mechanism that most AMPs utilize to kill bacteria. Comparatively, control polypeptide PL1 induced notable dye leakage at both pH 7.4 and 4.0, while PDL2 induced unappreciable dye leakage under both conditions, which well correlated to the helical and non-helical conformation of PL and PDL2, respectively (FIG. 7D). In support of the acid-activated membrane disruption, we further observed dramatic damage of the bacterial membranes by scanning electron microscopy (SEM) after incubation with PL2 at pH 4.0 (FIG. 2D). At pH 7.4, PL2 minimally affected the bacterial morphology, in consistence with its minimal membrane activity at the non-helical state. Control polypeptide PL1 showed membrane disruption towards SS1 at both pH 7.4 and 4.0, while PDL2 did not affect the morphology of bacteria under both conditions (FIG. 7E). Taken together, these results indicate that HCT-AMPs are able to selectively kill bacteria under acidic condition via acid-triggered helix formation and helix-assisted bacterial membrane disruption.

The emergence of drug resistant *H. pylori* is the main reason for clinical treatment failure. The resistance to clarithromycin, metronidazole, tetracycline, fluoroquinolones, as well as rifamycin has become a serious issue. As such, we further tested the antibacterial activity of HCT-AMPs against clinically isolated strains, including clarithromycin-resistant J99A-7, J99A-11, J99C-8, and J99D-1 (FIG. 8D and FIG. 8E; Example 2). PL2 effectively killed over 90% of these bacterial strains at pH 3.0 after 1 h incubation at a concentration of 4.4 μM (FIG. 3A), which further substantiated its potency in overcoming the drug resistance toward effective anti-*H. pylori* therapy. OAC could not effectively kill drug resistant bacteria J99A-11 and J99D-1 at pH 7.4. It instead killed bacteria at pH 3.0 in a concentration-dependent manner (FIG. 3B, and FIG. 8F), which was also attributed to the bacterial killing effect of omeprazole (FIG. 3C, and FIG. 8G).

The application of AMPs is often hurdled by the short durations of antimicrobial activity due to their rapid digestion by endogenous proteases. The RA polypeptide, with densely packed hydrophobic side chains forming a hydrophobic cortex to protect the polypeptide backbone amide bonds, was shown to be more stable against proteolysis compared to typical AMPs. We herein also tested the proteolytic stability of HCT-AMPs against pepsin, the main digestive protease in the stomach. After incubation with pepsin at pH 4.0 for up to 24 h, HPLC analysis showed that PL2 was resistant to pepsin-mediated degradation (FIG. 10; Example 2).

Figure 4:
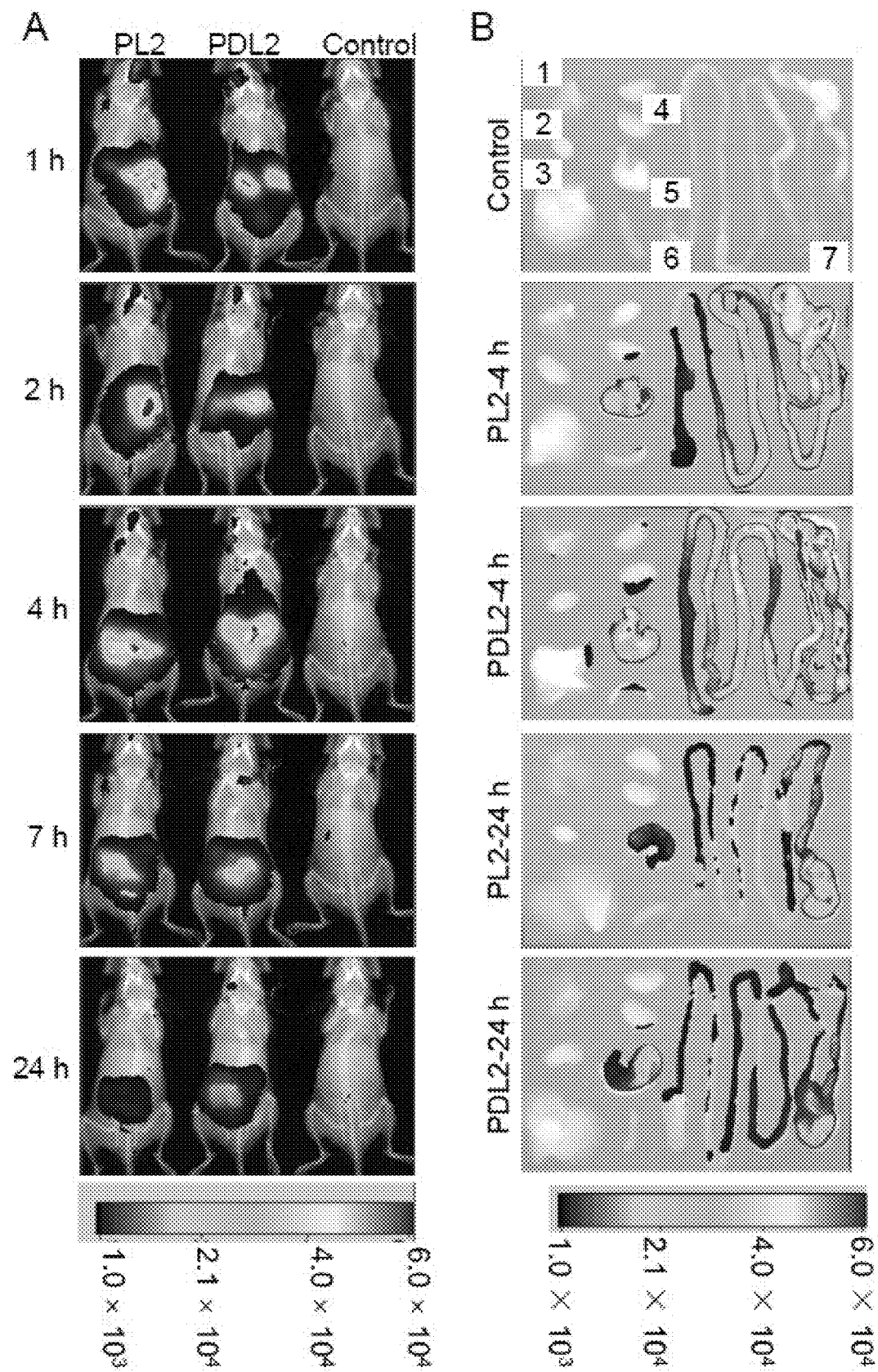
FIG. 4. In vivo distribution of Cy5-labeled HCT-AMPs following oral gavage. (A) Representative whole-body fluorescence imaging of C57BL/6J mice treated with Cy5-PL2 and Cy5-PDL2 (2.6 µmol/kg). Cy5-PL2, Cy5-PDL2 and PBS were administrated by oral gavage. Mice were then imaged with the Bruker Xtreme In-Vivo Fluorescence Imaging System at 1 h, 2 h, 4 h, 7 h, and 24 h post injection (p.i.). (B) Representative ex vivo fluorescence imaging of major organs (1, 2, 3, 4, 5, 6 and 7 represents lung, heart, liver, kidney, stomach, spleen, and intestines, respectively) from C57BL/6J mice treated with Cy5-PL2 and Cy5-PDL2. Major organs were harvested and imaged ex vivo 4 h or 24 h p.i. of Cy5-PL2 and Cy5-PDL2. (C) Ex vivo fluorescence intensity of stomach harvested from mice receiving the treatment in (B). Ex vivo images were quantified by measuring fluorescent intensity at selected region of interest (ROI). All values were expressed as means±standard deviation (n=3). (D) Retention of Cy5-PL2 and Cy5-PDL2 in mouse stomach 4 h and 24 h after oral gavage. Stomach samples were harvested and homogenized, and the lysates were used to determine the amount of Cy5 retained in the tissues with a fluorescence spectrometer. (E) Confocal image of mouse stomach following treatment with Cy5-PL2.
Figure 4:
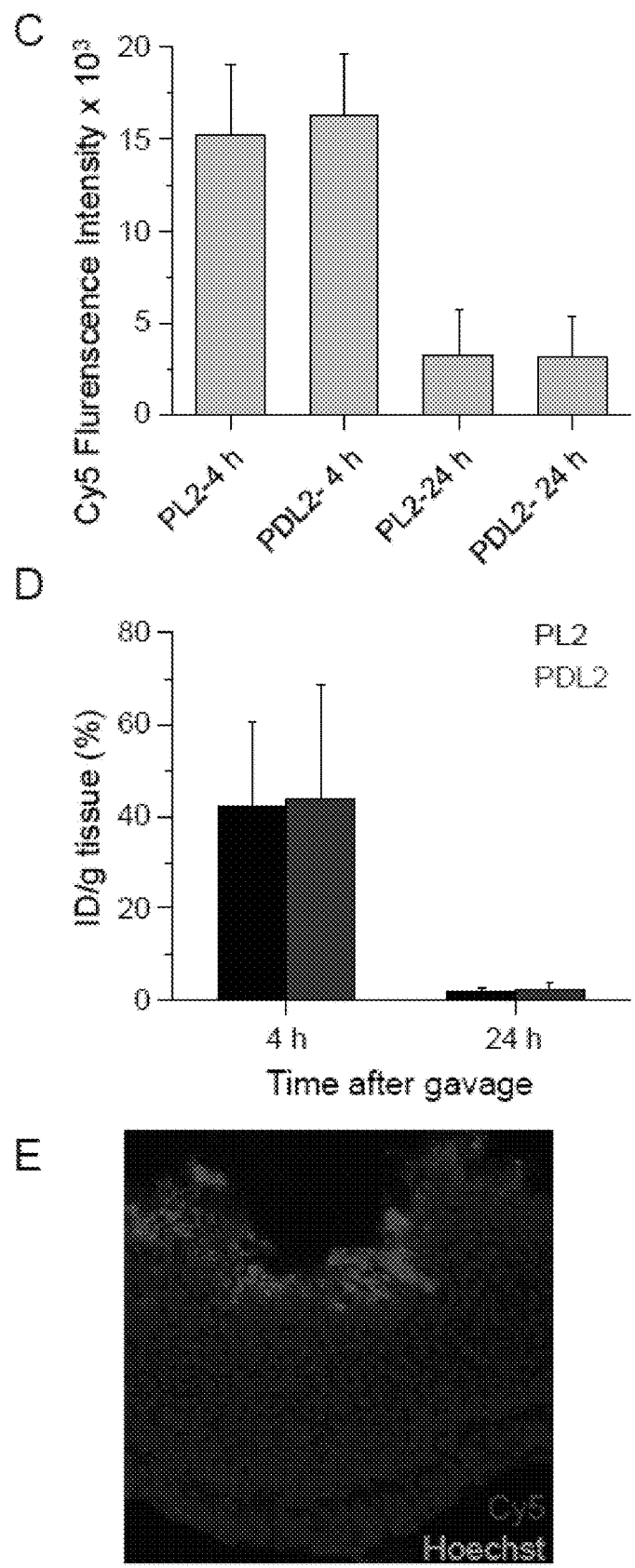

HCT-AMPs selectively kill *H. pylori* in vivo. We then evaluated the therapeutic efficacy of HCT-AMPs against *H. pylori* SS1 in vivo. We first studied the biodistribution of HCT-AMPs after oral gavage of Cy5-labeled polypeptides. PL2 and PDL2 showed similar biodistribution profiles, with majority of the polypeptides retained in the stomach and intestines within 4 h and gradually excreted within 24 h (FIG. 4A) (see also, Xiong et al., *Proc Natl Acad Sci USA*. 2017 Nov. 28; 114(48):12675-12680). By collecting major organs 4 h post oral gavage, we further observed strong fluorescence in the gastric tissue (FIGS. 4B and 4C). Such observation was further supported by the quantification of the gastric retention of PL2, which reached ~40% ID/g 4 h post gavage and notably decreased to ~6% 24 h post gavage (FIG. 4D). It should be mentioned that 4 h is a relatively long time compared with the reported gastric emptying time of mice. As such, these results indicate that HCT-AMPs could be effectively retained in the stomach against gastric emptying, likely due to the electrostatic interactions between the anionic mucus and the polypeptides that possess positive charges under acidic condition. We further studied the penetration of Cy5-PL2 into gastric mucosa by observing the cryosections of mouse stomach collected 4 h after oral gavage. The confocal image revealed a thin layer of Cy5-PL2 on the luminal side of the gastric mucosa, confirming the diffusion of PL2 toward the gastric epithelium and its retention in the mucus layer (FIG. 4E).

We then infected mice with *H. pylori* SS1 ($1\times10^8$ CFU/animal) by oral gavage every other day for four times (FIG. 5A). Two weeks after inoculation, infected mice were divided into four groups and treated with PBS (control), triple therapy OAC (omeprazole, amoxicillin, and clarithromycin), PDL2, or PL2. PL2 showed similar bacteria killing ability as the OAC treatment, with a decrease of bacterial burden by ~100 times as compared with the control group. PDL2, although displaying similar biodistribution profiles as PL2, showed no significant decrease of bacterial burden (FIG. 5B). These results indicate that the formation of membrane-active helical structure is essential for killing *H. pylori*. Because the pH in the mouse stomach (~3.0 when fed and ~4.0 when fasted) is higher than that in the human stomach, it is expected that the HCT-AMPs will show even higher *H. pylori* killing efficiency in the human stomach.

The toxicity of PL2 was further explored. No obvious change of animal body weight was noticed following treatment with PL2 as described above, indicating the low toxicity of PL2 in vivo (FIG. 5C). To analyze the toxicity of PL2 towards the stomach, we performed H&E-staining assay, the terminal deoxynucleotidyl transferase dUTP nick end labeling (TUNEL) assay, and detected caspase 3/8 activity of mouse stomach after treatments. No significant inflammation of stomach or injury of mucosa layer was observed after gavage of PL2 according to the H&E-staining assay (FIG. 11A-C; Example 2). PL2 administration did not induce apoptosis in stomach cells, as measured by the TUNEL assay and the activities of caspase 3 and 8 (FIG. 11D-G). The plasma levels of alanine aminotransferase, aspartate aminotransferase, creatinine, urea nitrogen, sodium ion, and potassium ion showed no significant change after the PL2 treatment (Table 2), verifying the lack of significant acute damage toward the liver and kidney as well as the balance of electrolytes in the blood. The low toxicity of PL2 was further confirmed by H&E staining of intestines, liver, and kidney, with barely detectable histological abnormality (FIG. 12; Example 2). More importantly, PL2 did not cause undesired killing of the commensal bacteria in the ileal contents and feces of mice, while OAC treatment killed commensal bacteria in the ileal contents and feces by 65% and 86%, respectively (FIG. 5D). These results collectively indicate the low side effect of HCT-AMPs toward normal cells or commensal bacteria.

TABLE 2

The toxicity of PL2 after oral gavage.

| Treatment | ALT (U/L) | AST (U/L) | Creatinine (μM) | Urea nitrogen (mM) | Potassium ion (mM) | Sodium ion (mM) |
|---|---|---|---|---|---|---|
| NS | 32.6 ± 4.5 | 132.3 ± 23.3 | 9.7 ± 1.2 | 8.2 ± 0.4 | 8.4 ± 0.4 | 150.2 ± 0.7 |
| 5% DMSO | 36.0 ± 12.7 (P = 0.3) | 123.0 ± 30.6 (P = 0.2) | 9.7 ± 2.0 (P = 0.5) | 8.6 ± 1.7 (P = 0.4) | 8.6 ± 1.1 (P = 0.4) | 151.7 ± 2.2 (P = 0.2) |
| OAC | 31.6 ± 2.9 (P = 0.4) | 83.6 ± 4.5 (P = 0.02) | 9 ± 1.4 (P = 0.3) | 7.6 ± 0.3 (P = 0.09) | 7.2 ± 0.2 (P = 0.01) | 145.5 ± 2.6 (P = 0.04) |
| PL2 | 37.3 ± 0.5 (P = 0.1) | 120.3 ± 17.9 (P = 0.1) | 8.7 ± 0.9 (P = 0.1) | 6.8 ± 0.6 (P = 0.03) | 8.1 ± 0.2 (P = 0.05) | 149.4 ± 1.6 (P = 0.2) |

[a] Effect of PL2 (2.6 μmol/kg) on liver and kidney functions as well as balance of electrolytes in the blood. Physiological saline (NS), 5% DMSO and OAC were served as control groups. Data are presented as mean ± SD (n = 3) and analyzed by student t test as compare with NS. P > 0.05 means statistical insignificance, and P ≤ 0.05 means statistical significance.

Thus, we developed a class of pH-sensitive HCT-AMPs as a single therapeutic agent to target and selectively treat *H. pylori* infection in the stomach. The HCT-AMPs can specifically kill *H. pylori*, including drug-resistant strains, under acidic conditions, and showed minimal toxicity against normal tissues/commensal bacteria. The pH-sensitive HCT-AMPs greatly outperform the triple therapy that suffers from undesired toxicity as well as drug resistance. This strategy therefore provides a safe and effective approach to overcome the critical challenges in the treatment of *H. pylori*-induced gastric diseases, and would render promising utilities toward anti-*H. pylori* therapy.

Embodiments of the Invention

Considering that *H. pylori* thrive in the stomach under unique acidic condition (with a mean gastric pH of ~2 in human) while commensal bacteria reside in the intestine with relatively neutral pH (6-8), we herein developed a class of pH-sensitive, helix-coil conformation transitionable antimicrobial polypeptides (HCT-AMPs), including (PGA)$_m$-r-(PHLG-MHH)$_n$, with both anionic groups (e.g., glutamic acid) and cationic groups (e.g., tertiary amine) in the polypeptide side chains (FIG. 1A). The HCT-AMPs display distorted helix at physiological pH due to the intramolecular electrostatic interactions between the anionic carboxylate and cationic amine groups, ultimately leading to minimal toxicity to intestinal commensal bacteria. While under the acidic condition in the stomach, the HCT-AMPs transform to the helical conformation due to the protonation of the carboxylate groups and the depletion of the side-chain electrostatic interaction, which result in potent antimicrobial efficacy against *H. pylori* in the stomach. These HCT-AMPs showed comparable *H. pylori* killing efficacy as clinically used triple therapy in a mouse model, with inhibited toxicity against normal tissues and commensal bacteria as oppose to undesired killing of 65-86% of commensal bacteria in the ileal contents and feces in the triple therapy.

The monomers of the polypeptides described herein are typically natural amino acids, such as glutamic acid or aspartic acid, however the amino acids can also be non-natural amino acids such as β-amino acids, γ-amino acids, δ-amino acids, or other known non-natural amino acids. Accordingly, the disclosure provides the formula described herein wherein the amino acid backbone units of the formulas can be replaced with β-amino acid, γ-amino acid, δ-amino acid moieties.

The polypeptides of the formulas described herein can terminate in carboxy groups at their C terminus (e.g., where the Formulas are substituted at the carbonyl of the polypeptides backbone chain with —OH), and the polypeptides can terminate in amino groups or nitrogen protecting groups at their N terminus (e.g., where the Formulas are substituted at the amine of the polypeptides backbone chain with —H, -Cbz, or the like). As would be readily recognized by one skilled in the art, the C termini and N termini (groups at the end of the bond at each end of the polyamides of the Formulas) can also be suitable carboxy or amino protecting groups, respectively. Examples of such groups include the various R groups and protection strategies described by Greene and Wuts (*Protective Groups in Organic Synthesis*, 3$^{rd}$ Ed., John Wiley & Sons, Inc., 1999, which is incorporated herein by reference in its entirety), as well as the carboxy or amino protecting groups described by Kocienski (*Protecting Groups*, Georg Thieme Verlag Stuttgart, New York, 1994, which is incorporated herein by reference in its entirety).

The polypeptides can comprise random or block copolymers. However, the polypeptides of the formulas described herein are random copolymers, as shown by the "r" over the bond between the m and n units of the polypeptides (as would be readily recognized by the method of preparation of the polypeptides as described in Example 1). Thus, the arrangement of the m units and n units is random throughout the length of the polypeptides of the formulas, and the total number of m units and n units is defined by m and n for each formula, randomly arranged along the length of the polypeptide.

The invention thus provides an antimicrobial polypeptide comprising Formula I:

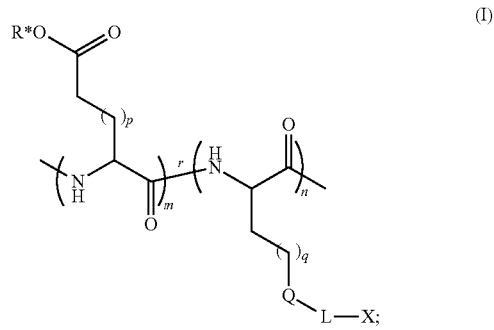

wherein
m is 3 to about 50;
n is 5 to about 100;
p is 0 or 10:
q is 0, 1, 2, or 3;
R* is H or a negative charge;
Q is —C(=O)O—, —C(=O)NH—, —NH—C(=O)—, or a direct bond;
L is a carbon-containing linker of at least two atoms in length, and wherein the atom connecting to X is a carbon atom; and
X is primary amine, a secondary amine, a tertiary amine, or a quaternary ammonium moiety. The polypeptide adopts a random coil confirmation in solution at physiological pH, and the polypeptide adopts a helical confirmation in solution in the stomach of a mammal. In one embodiment, the polypeptide adopts a random coil confirmation in solution at a pH of greater than about 6.5, and the polypeptide adopts a helical confirmation in solution at a pH of less than about 3.5. In another embodiment, the polypeptide adopts a random coil confirmation in solution at a pH of greater than about 5, and the polypeptide adopts a helical confirmation in solution at a pH of less than about 4.5.

In further embodiments, the polypeptide comprises Formula II:

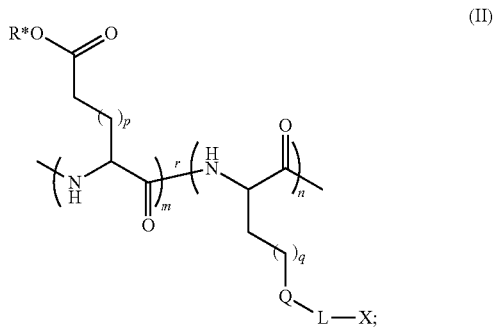

wherein
m is 3 to about 40;
n is 5 to about 80;
p is 0 or 1;
q is 0, 1, 2, or 3;
R* is H or a negative charge;
Q is —C(=O)O—, —C(=O)NH—, —NH—C(=O)—, or a direct bond;

L is a carbon-containing linker of two to twenty atoms in length; and

X is an aliphatic or aromatic quaternary ammonium moiety.

In yet further embodiments, the polypeptide comprises Formula III or Formula IV:

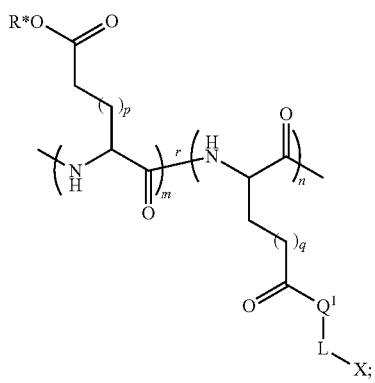

(III)

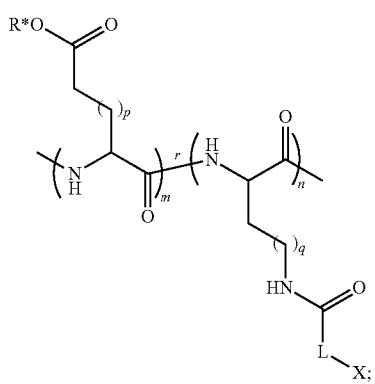

(IV)

wherein $Q^1$ is O or NH.

In additional embodiments, the polypeptide is or comprises Formula V:

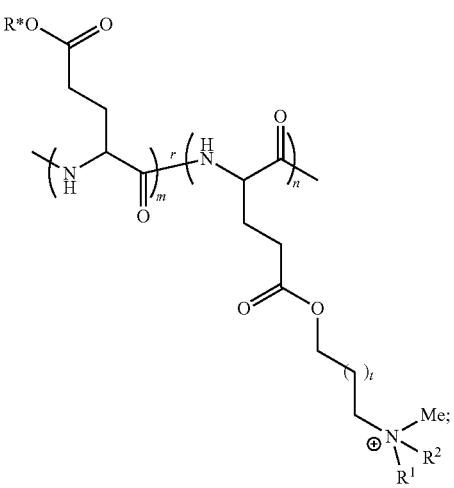

(V)

wherein m is about 3 to about 40, n is about 5 to about 80, t is about 1 to 8, and $R^1$ and $R^2$ are each independently $(C_2-C_8)$alkyl.

The total m units can be 3 to about 40, about 5 to about 30, or about 10 to about 20; and the total n units can be about 5 to about 80, about 5 to about 50, about 8 to about 40, or about 10 to about 20, noting that the polypeptide is a random polymer polypeptide and the m and n units of the formulas are randomly dispersed and not blocks, although occasionally 2-4 m or 2-4 n units may randomly align together.

In various embodiments, p can be 0, 1, 2, 3, 4, 5, 6, 7, 8, 9, or 10, or a range from any one to another of the aforementioned integers, depending on the base amino acid chosen and any synthetic modifications performed prior to formation of the polypeptide.

In various embodiments, the polypeptide has low toxicity at neutral pH and has high antibacterial activity against *H. pylori* in an environment having a pH of less than about 4.4.

The invention also provides a method comprising treating a bacterial infection in the stomach of a subject in need thereof by administering to the subject a therapeutically effective amount of a polypeptide described herein, wherein the bacterial infection is thereby treated. The polypeptide can be administered orally, and the bacterial infection can be one caused by *H. pylori*.

In some embodiments, the subject has been diagnosed with gastritis, a gastric ulcer, or gastric carcinoma. In various embodiments, the polypeptide causes killing of less than 50% of commensal bacteria in the ileal contents, and typically little or no killing at all, due to the near neutral pH of the intestines. The present disclosure thus provides a method of treating a bacterial infection in the stomach of a subject, the method comprising administering to the subject a therapeutically effective dose of a polypeptide or polypeptide composition described herein. In one embodiment, the bacterial infection is from *H. pylori*. The antimicrobial polypeptide can be included in a therapeutic composition, for example, an aqueous composition optionally including isotonic agents, buffering agents, and the like.

Linking Group L

The linking group, L, is not necessarily critical for the function of the antimicrobial polypeptide but should be a chain of atoms that allows group X to be separated from the polypeptide backbone by at least 5 linear atoms, or by at least 6 linear atoms, and for example, up to about 20 linear atoms. The nature of L is such that it allows the polypeptide to adopt a distorted helix at physiological pH due to the intramolecular electrostatic interactions between the anionic carboxylate and neutral or cationic amine groups, and to adopt a helical conformation due to the protonation of the carboxylate groups and the depletion of the side-chain electrostatic interaction while under the acidic condition, such as in the stomach. Thus, in various embodiments, the side chain having a positively charged nitrogen, or a nitrogen able to form a positive charge in an acidic environment, can be separated from the polypeptide backbone by at least 5 linear atoms to about 20 linear atoms. For example, the linking group, L, can separate the nitrogen or ammonium moiety from the backbone by 6, 7, 8, 9, 10, 11, 12, 13, 14, 15, 16, 17, 18, 19, or 20 linear atoms.

The linking group L can be, for example, a carbon chain of about 4 to about 20 atoms in length, where the chain is optionally interrupted by phenyl, benzyl, ester, amide, —C═C—, —C≡C—, phosphoester, phosphoamide, or oxyethylene groups, the chain can be linear or branched, and the chain can be optionally substituted, for example, with halides, oxo groups (═O), or hydroxyl groups, or by other groups described herein as substituents.

In various embodiments, linking group L can be a divalent radical of the formula —W-A-W— wherein each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CH$_2$)$_n$— where n is 1-10, or a direct bond; wherein each R' is independently H, (C$_1$-C$_6$)alkyl, or a nitrogen protecting group; and A is (C$_1$-C$_{20}$)alkyl, (C$_2$-C$_{16}$)alkenyl, (C$_2$-C$_{16}$)alkynyl, (C$_3$-C$_5$)cycloalkyl, (C$_6$-C$_{10}$)aryl, —(OCH$_2$—CH$_2$)$_n$— where n is 1 to about 20, —C(O)NH(CH$_2$)$_n$ wherein n is 1 to about 6, —(CH$_2$)$_n$—N(Me)(CH$_2$)$_n$ wherein each n is 1 to about 6; or (C$_1$-C$_{20}$)alkyl, (C$_2$-C$_6$)alkenyl, (C$_2$-C$_{16}$)alkynyl, or —(OCH$_2$—CH$_2$)$_n$— optionally interrupted between two carbons, or between a carbon and an oxygen, with a (C$_3$-C$_8$)cycloalkyl, heterocycle, or (C$_6$-C$_{10}$)aryl group; wherein the chain of L is optionally substituted by one, two, three, four, or five oxo groups, hydroxy groups, (C$_1$-C$_4$)alkyl groups, heterocycle or heteroaryl groups such as pyridine groups, piperidine groups, pyrrolidine groups, monosaccharide groups, or a combination thereof. For example, L can be a (C$_6$-C$_{20}$)alkyl group optionally interrupted by one, two, three, or four nitrogen atoms, oxygen atoms, phenyl groups, or a combination thereof, and wherein the (C$_6$-C$_{20}$)alkyl group is optionally substituted by one, two, three, four, or five oxo groups, hydroxy groups, (C$_1$-C$_4$)alkyl groups, pyridine groups, piperidine groups, pyrrolidine groups, monosaccharide groups, or a combination thereof.

In certain embodiments, L is (C$_2$-C$_{12}$)alkyl, wherein the (C$_2$-C$_{12}$)alkyl is optionally interrupted with one to five oxygen atoms, sulfur atoms, or a combination thereof, and optionally interrupted with phenyl, cycloalkyl, heterocycle, or heteroaryl.

The term "interrupted" indicates that another group is inserted between two adjacent carbon atoms of a particular carbon chain being referred to in the expression using the term "interrupted", provided that each of the indicated atoms' normal valency is not exceeded, and that the interruption results in a stable compound. Suitable groups that can interrupt a carbon chain of L in the formulas described herein include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) sulfonyl (SO$_2$), and PEG. Alkyl groups can be interrupted by one or more (e.g., 1, 2, 3, 4, 5, or about 6) of the aforementioned suitable groups, in various embodiments. The site of interruption can also be between a carbon atom of an alkyl group and a carbon atom to which the alkyl group is attached.

Techniques for preparing linking groups L are standard transformations and are well known in the art. Such techniques are described by, for example, by Greg T. Hermanson in Bioconjugate Techniques, Academic Press, San Diego, Calif. (1996). Linking groups L can be alkyl or alkoxy chains, such as (C$_1$-C$_6$)alkyl or (C$_1$-C$_6$)alkoxy groups. Certain linking groups L and methods for preparing the covalent linkages are described in, for example, U.S. Pat. No. 7,282,339 (Beechem et al.); in *Peptides: Chemistry and Biology* by Sewald and Jakubke, Wiley-VCH, Weinheim (2002), pages 212-223; and in *Organic Synthesis on Solid Phase* by Dorwald, Wiley-VCH, Weinheim (2002); the techniques of which are incorporated herein by reference.

In certain specific embodiments, L is (C$_2$-C$_{12}$)alkyl, —CH$_2$-Ph-(CH$_2$)$_y$— wherein y is 1 to about 4, —CH$_2$-Ph-O—(CH$_2$)$_2$—O—(CH$_2$)$_2$—, —CH$_2$-Ph-O—(CH$_2$)$_2$—S—(CH$_2$)$_2$—, —CH$_2$-Ph-O—(CH$_2$)$_3$—O—(CH$_2$)$_2$—, —CH$_2$-Ph-O—(CH$_2$)$_3$—S—(CH$_2$)$_2$—, or —CH$_2$-Ph-O—CH$_2$—CH(S(CH$_2$)$_2$—X)—CH$_2$—S—(CH$_2$)$_2$—.

Ammonium Groups and Nitrogens that are Cationic Under Acidic Conditions (Group X)

The group X can be an aliphatic or aromatic amine, or aliphatic or aromatic quaternary ammonium moiety, in various embodiments. For example, X can be —N$^+$(R)$_3$ wherein each R is independently phenyl or a straight chain or branched (C$_1$-C$_{10}$)alkyl. In certain embodiments, the total number of carbon atoms in X (e.g., the three R groups combined) is 3 to about 18, preferably 5 to about 15. In certain specific embodiments, X is:

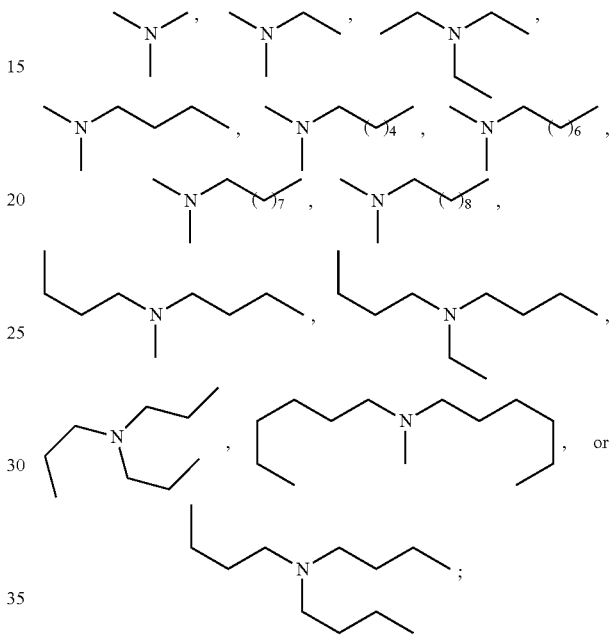

wherein X is bonded to L at the nitrogen of X to form a quaternary ammonium moiety.

X can also be an aromatic quaternary ammonium moiety selected from nitrogen heterocycles recited herein, for example:

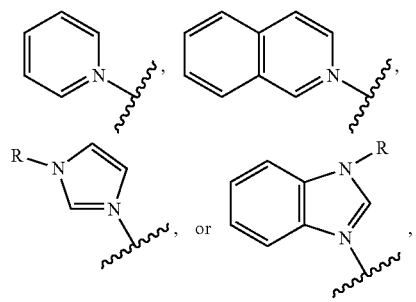

wherein R is H or (C$_1$-C$_{10}$)alkyl.

The group X can be any moiety that includes a nitrogen cation, for example, at a pH of 1 to about 4.5. The X group can be a moiety having a positive charge on a nitrogen heteroatom, where the heteroatom is part of a linear chain or part of a heterocycle. For example, the cationic nitrogen atoms can be a group such as protonatable nitrogen non-heterocycles (e.g., primary amines, secondary amines, tertiary amines, quaternary ammonium groups, guanidino groups (—NH(C=NH)—NH$_2$) (such as for an arginine monomer), hydrazones (—C(=N—NH$_2$)—R where R is H or alkyl), hydrazides (—C(=O)(—NH—NH$_2$)), hydrazines (—NH—NH$_2$)), or protonatable nitrogen heterocycles (e.g., aniline, indole, piperidine, pyridine, pyrimidine, pyrrolidine, pyrrole, imidazole, or the like). For Formulas I-IV, guanidino, hydrazones, hydrazides, and hydrazines are considered primary amines. See Lu et al., *Nature Commun.*, 2011, 2, 206 and U.S. Pat. No. 9,243,040 (Cheng et al.) for useful amino acid monomers with side chains that include a protonatable nitrogen moiety.

In various embodiments, the X moiety can be any protonated primary, secondary, or tertiary amine, where the secondary and tertiary amines are substituted by, for example, (C$_1$-C$_{12}$)alkyl groups, or benzyl groups. The moiety can also be a group that includes a quaternary ammonium cation, such as a protonated nitrogen heteroaryl group. Examples of nitrogen heteroaryl groups that can be protonated include pyridine, imidazole, triazole, and the like (e.g., to form pyridinium cations, imidazolium cations, and triazolium cations). In various embodiments, the X moiety can include one to ten carbon atoms and at least one N, for example, as necessary to form a moiety with an ammonium cation or a guanidinium cation.

Other polypeptide units can be prepared as described by U.S. Pat. No. 9,243,040 (Cheng et al.) and PCT Publication No. WO2016/210442 (Cheng et al.), which are incorporated herein by reference. Such polypeptide units can be used in the antimicrobial polypeptides described herein.

General Synthetic Methods

In general, preparation of the compounds and formulas described herein, and modifications thereof, can be made according to organic synthesis techniques known to those of skill in the art and/or according to the synthetic schemes provided herein. Where desired, synthesis of a subject compound can begin with commercially available chemicals, from compounds described in the chemical literature, or from products of the reactions and methods described herein. Commercially available compounds may be obtained from standard commercial sources including Acros Organics (Pittsburgh, Pa.), Aldrich Chemical (Milwaukee, Wis., including Sigma Chemical and Fluka), Eastman Organic Chemicals, Eastman Kodak Company (Rochester, N.Y.), Fisher Scientific Co. (Pittsburgh, Pa.), ICN Biomedicals, Inc. (Costa Mesa, Calif.), Lancaster Synthesis (Windham, N.H.), Spectrum Quality Product, Inc. (New Brunswick, N.J.), TCI America (Portland, Oreg.), Combi-Blocks, Inc. (San Diego, Calif.), Oakwood Products, Inc. (Estill, S.C.), and Wako Chemicals USA, Inc. (Richmond, Va.).

In addition, methods known to one of ordinary skill in the art may be identified through various reference books and databases. Suitable reference books and treatises that detail the synthesis of reactants useful in the preparation of the inhibiting agents described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992; and *Protecting Groups in Organic Synthesis, Second Edition*, Greene, T. W., and Wutz, P. G. M., John Wiley & Sons, New York.

Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

A number of exemplary methods for preparation of the compounds of the invention are provided below. These methods are intended to illustrate the nature of such preparations are not intended to limit the scope of applicable methods. Other variations, such as adding various substituents (e.g., as defined above) on various alkyl, aryl, or heterocycle groups are included in the scope of the invention. Relevant starting materials can typically be purchased from the commercial suppliers cited above (e.g., from Sigma-Aldrich) or they can be prepared in a few standard steps from commercially available materials.

The polypeptides described herein can be prepared, for example, as illustrated above in Scheme 1. As would be readily recognized by one of skill in the art, the methods can be varied to provide a wide range of polypeptides of Formula I. Various N-carboxyanhydrides (NCA) can be prepared to provide the random polymer polypeptides of the formulas described herein. Examples of useful NCAs include the following. Polypeptides with an aromatic ring in the side chain can be synthesized based on monomers such as:

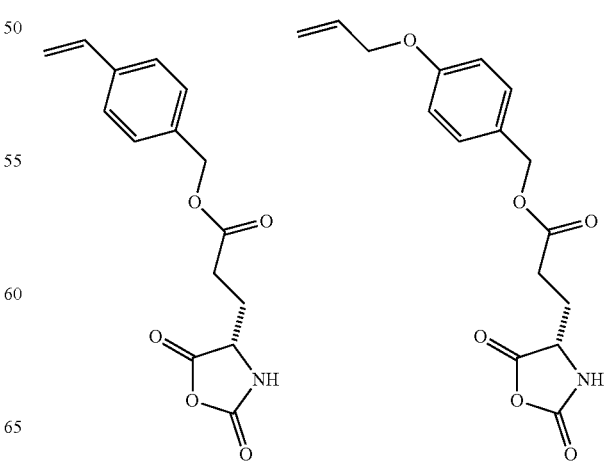

Scheme A1.

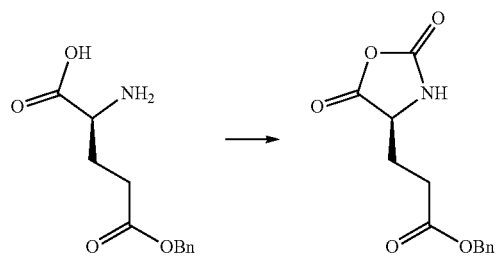

Scheme A2.

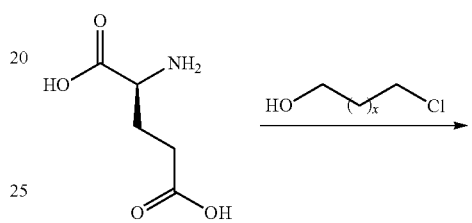

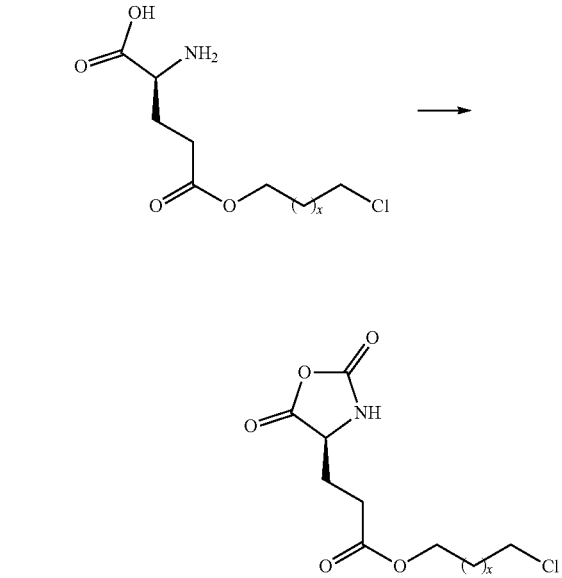

where x is 0 to about 16.

Scheme A3.

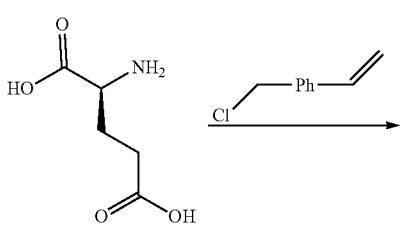

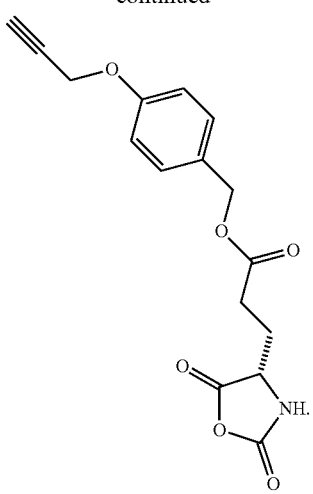

Polypeptides based on lysine can be synthesized based on the monomer such as:

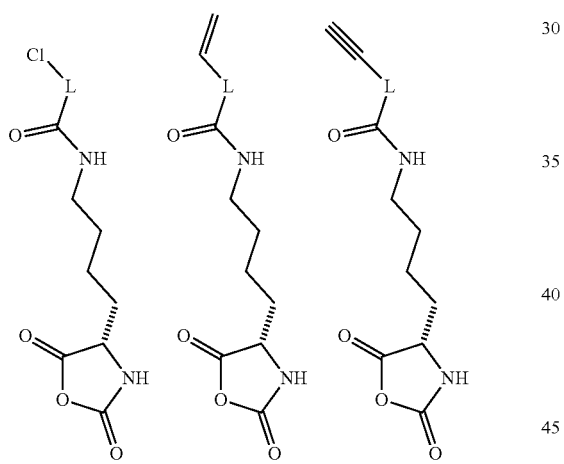

where L is as defined for Formula I. A chloride or other leaving group can be displaced with an amine group X, and alkene and alkyne groups can be functionalized to provide amine group X, or they can be reacted with an azide group to form a heterocycle-containing linking group, wherein the azide starting material has an amine group X in the molecule. Examples of specific L groups include $(C_2$-$C_{12})$alkyl, —$CH_2$-Ph-$(CH_2)_y$— wherein y is 1 to about 4, —$CH_2$-Ph-O—$(CH_2)_2$—O—$(CH_2)_2$—, —$CH_2$-Ph-O—$(CH_2)_2$—S—$(CH_2)_2$—, —$CH_2$-Ph-O—$(CH_2)_3$—O—$(CH_2)_2$—, —$CH_2$-Ph-O—$(CH_2)_3$—S—$(CH_2)_2$—, or —$CH_2$-Ph-O—$CH_2$—CH(S$(CH_2)_2$—X)—$CH_2$—S—$(CH_2)_2$—.

Methods for modifying amino acid side chains are known in the art. Suitable methods include forming an NCA and installing various linking groups L, or modifying a side chain and then forming an NCA, for example, as illustrated in the following schemes.

-continued
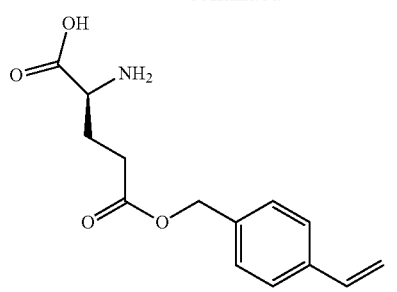
Scheme A5.
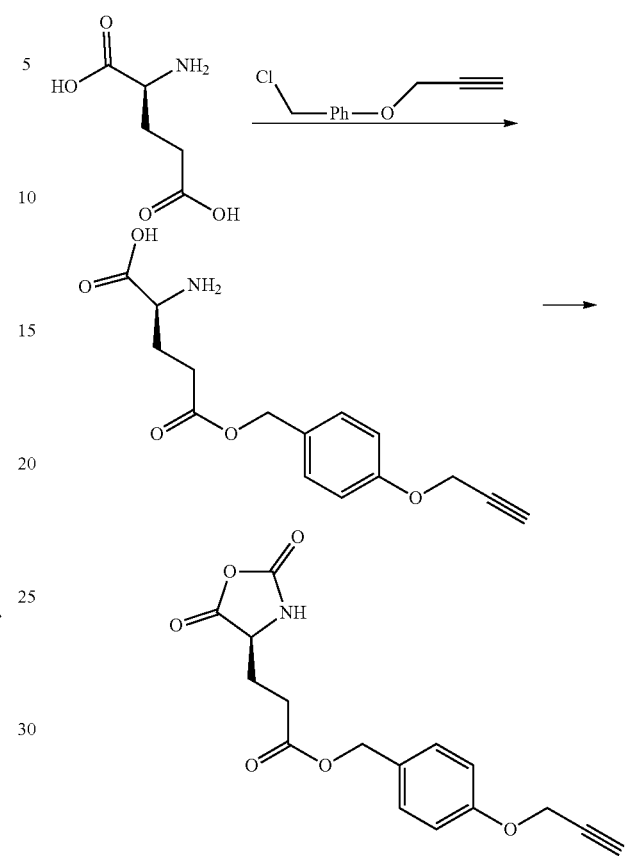
Scheme A4.
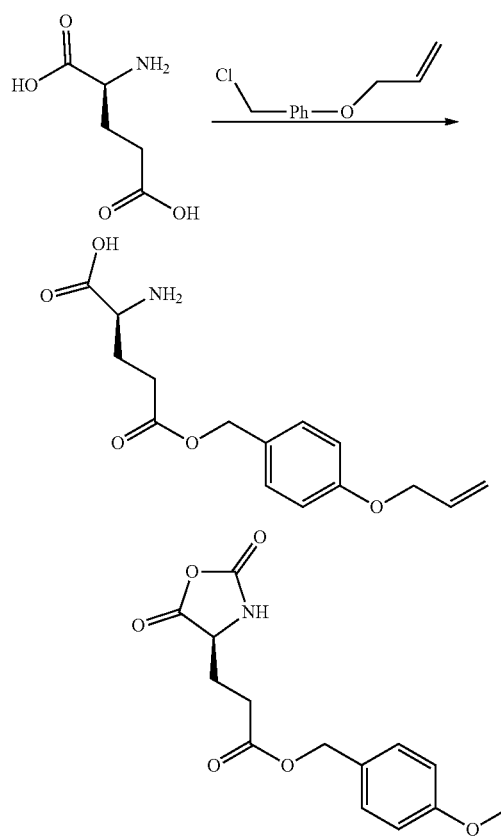
Scheme A6.
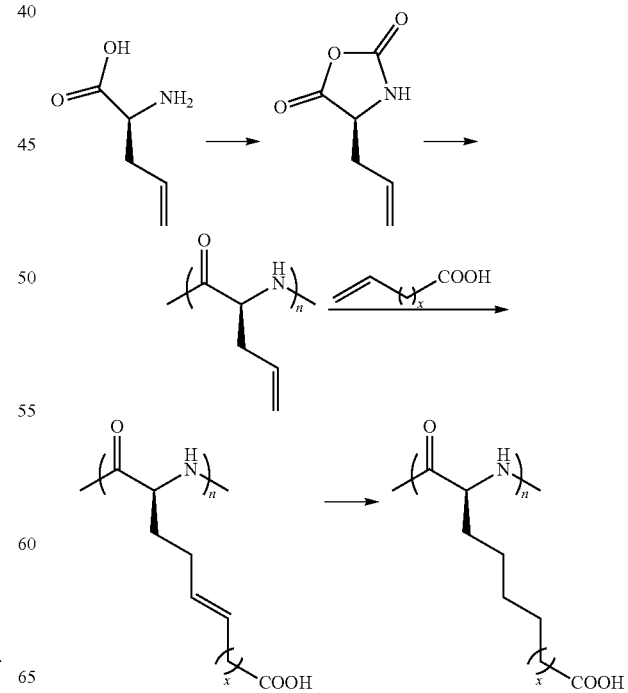

where n is 1 to about 100, typically 1 to about 5 or 10; and x is 1 to about 10. Metathesis can optionally be performed on the NCA monomer prior to forming a random polypeptide described herein.

Scheme A7.

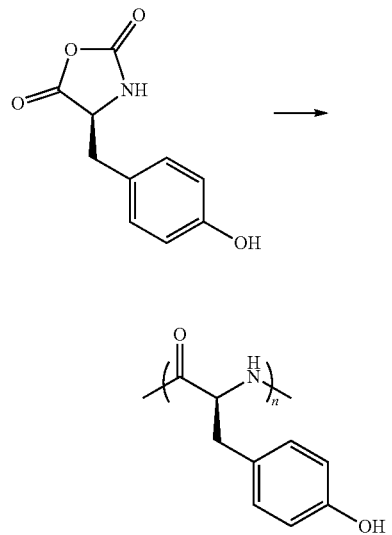

where x is 0 to about 16, and $R_1$-$R_3$ are H, Ph, Bn, or a straight chain or branched alkyl, such as a ($C_1$-$C_{10}$)alkyl. Functionalization of the phenol group can optionally be performed on the NCA monomer prior to forming a random polypeptide described herein.

Techniques for the preparation of amine-containing side chains are further illustrated in the following schemes, where the functionalization of the side chain can be performed prior to polymerization, or afterward, as appropriate for the specific polypeptide of interest.

Scheme B1.

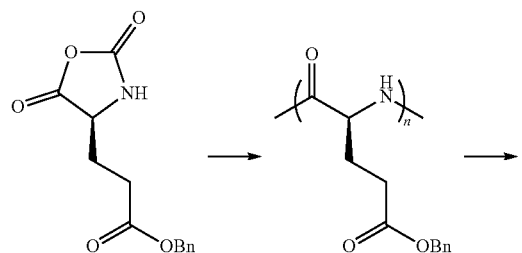

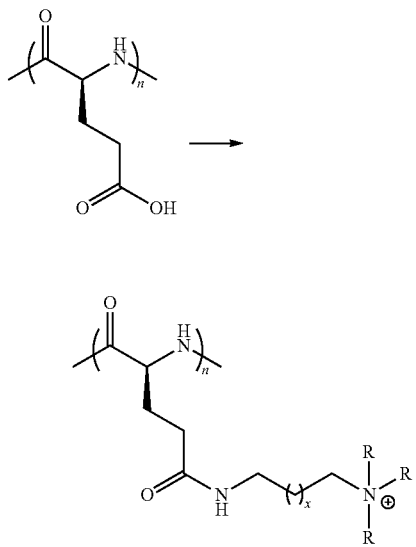

See Lu et al., *Nature Commun.*, 2011, 2, 206, the synthetic techniques of which are incorporated herein by reference.

Scheme B2.

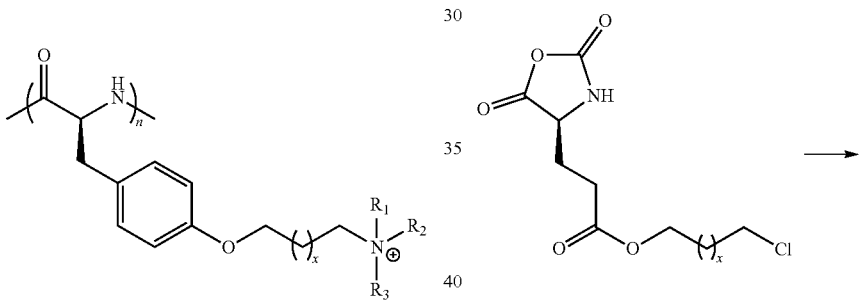

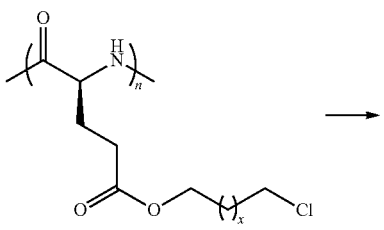

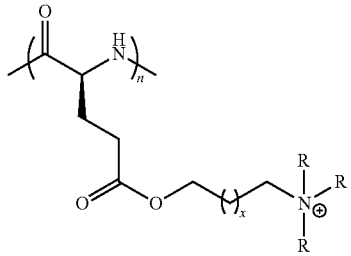

See Xiong et al., *PNAS*, 2015, 112, 13155-13160, the synthetic techniques of which are incorporated herein by reference.

Scheme B3.
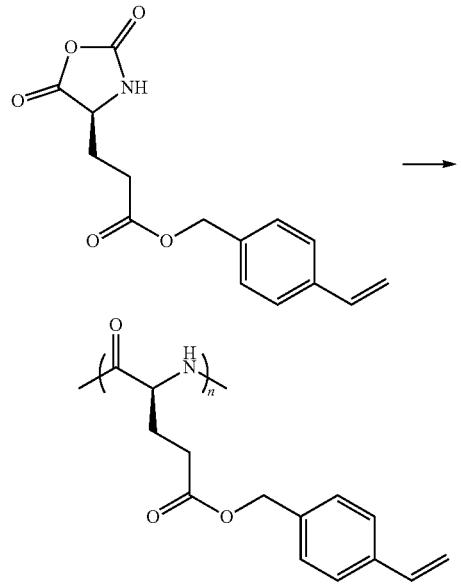
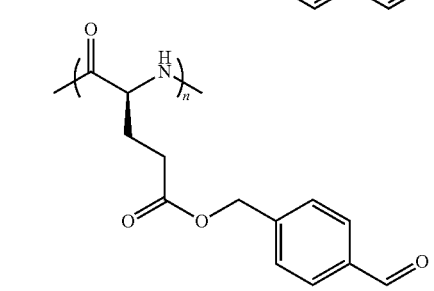
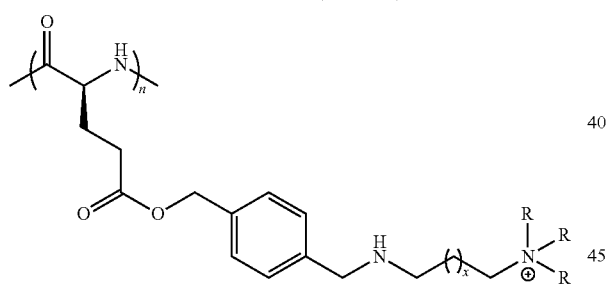
See Lu et al., *Macromolecules*, 2011, 44, 6237-6240, the synthetic techniques of which are incorporated herein by reference.
Scheme B4.
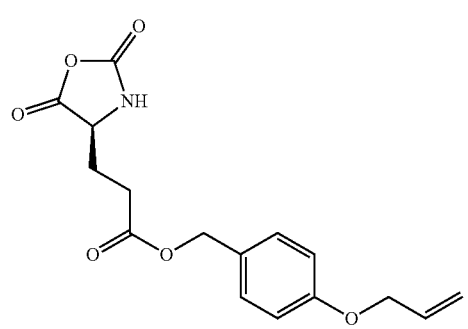
-continued
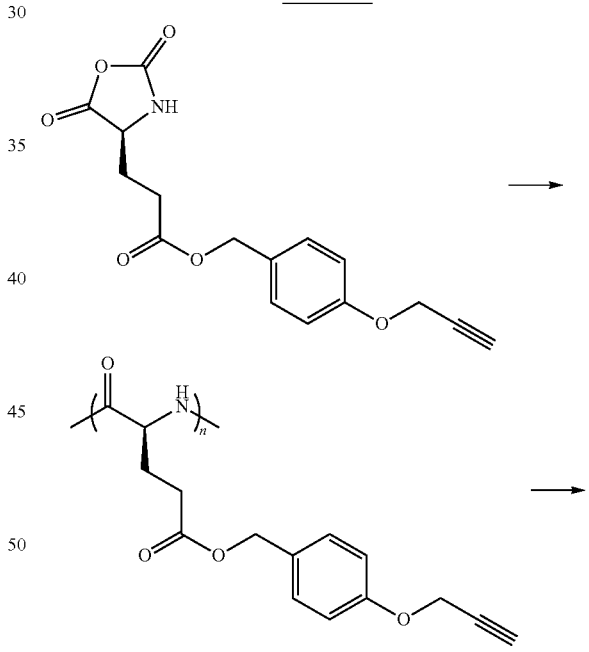
See Zhang et al., *Macromolecules*, 2011, 44, 6641-6644, the synthetic techniques of which are incorporated herein by reference.
Scheme B5.
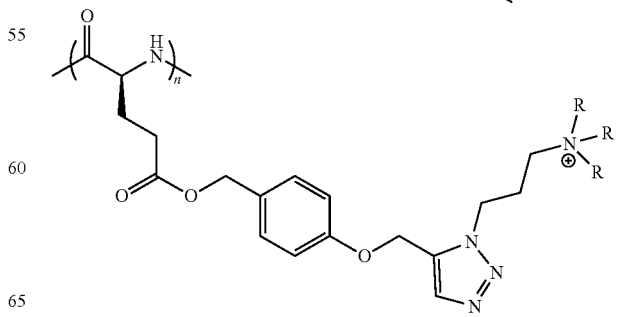

See Zhang et al., *Biomaterials*, 2014, 35, 3443-3454, the synthetic techniques of which are incorporated herein by reference.

Scheme B6.

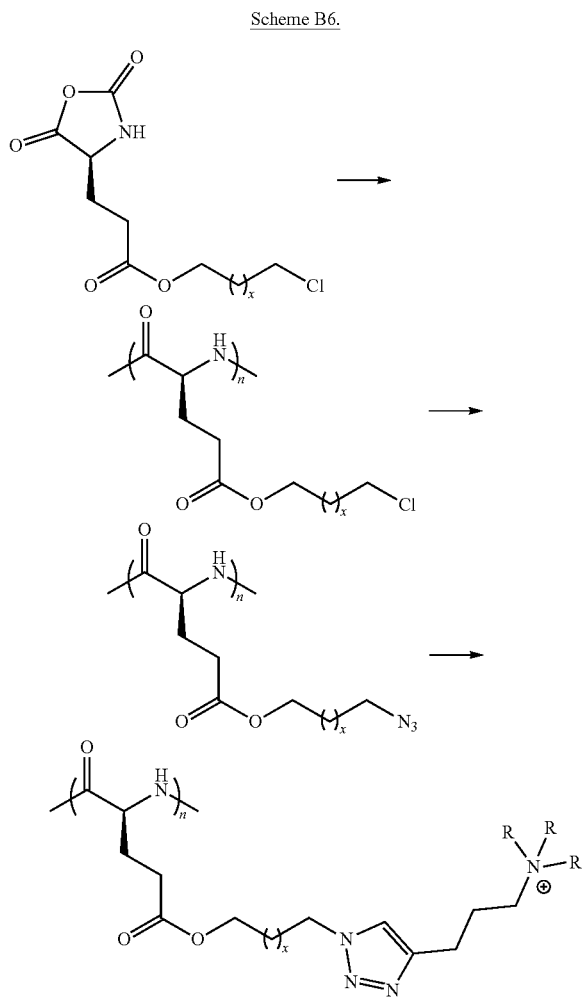

See Tang et al., *Chemical Science*, 2013, 4, 3839-3844, the synthetic techniques of which are incorporated herein by reference.

In Schemes B1-B6, the R groups on N can each independently be H, Ph, Bn, or a straight chain or branched alkyl, such as a $(C_1\text{-}C_{10})$alkyl, thereby forming an X group as defined for Formula I. Starting materials having suitable amine and ammonium groups are commercially available or can be prepared in a few steps using standard synthetic techniques.

Pharmaceutical Formulations

The polymers (e.g., polypeptides) described herein can be used to prepare therapeutic pharmaceutical compositions. The polymers may be added to the compositions in the form of a salt or solvate. For example, in cases where polymers are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The polymers of the formulas described herein can be formulated as pharmaceutical compositions and administered to a mammalian host, such as a human patient, in a variety of forms. The forms can be specifically adapted to a chosen route of administration, e.g., oral or in some cases by a feeding tube or the like.

The polymers described herein may be systemically administered in combination with a pharmaceutically acceptable vehicle, such as an inert diluent or an assimilable edible carrier. For oral administration, polymers can be enclosed in hard or soft-shell gelatin capsules, compressed into tablets, or incorporated directly into the food of a patient's diet. Polymers may also be combined with one or more excipients and used in the form of ingestible tablets, buccal tablets, troches, capsules, elixirs, suspensions, syrups, wafers, and the like. Such compositions and preparations typically contain at least 0.1% of active polymer. The percentage of the compositions and preparations can vary and may conveniently be from about 2% to about 60% of the weight of a given unit dosage form. The amount of active polymer or agent in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active polymers or composition may be incorporated into sustained-release preparations and devices.

Solutions of the active polymers, composition, or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms. A liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the compositions can be brought about by adding agents that delay absorption, for example, aluminum monostearate and/or gelatin.

Solutions can be prepared by incorporating the active compound in the required amount in the appropriate solvent with various other ingredients enumerated above, as desired, optionally followed by filter sterilization. In the case of sterile powders, methods of preparation can include vacuum drying and freeze-drying techniques, which yield a powder of the active ingredient plus any additional desired ingredient present in the solution.

Useful liquid carriers can include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as other antimicrobial agents can be added to optimize the properties for a given use.

Useful dosages of the polymers described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a polymers, or an active salt or derivative thereof, required for use in treatment will vary not only with the particular polymers or salt selected but also with the route of administration, the nature of the condition being treated, and the age and condition of the patient, and will be ultimately at the discretion of an attendant physician or clinician.

The polymers can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating a bacterial infection in a mammal, which involve administering to a mammal having a bacterial infection an effective amount of a polymer or composition described herein. A mammal includes a primate, human, rodent, canine, feline, bovine, ovine, equine, swine, caprine, bovine and the like.

The ability of a compound of the invention to treat a bacterial infection may be determined by using assays well known to the art. For example, the design of treatment protocols, toxicity evaluation, data analysis, quantification of tumor cell kill, and the biological significance of the use of these screens are known. In addition, ability of a polymer to treat a bacterial infection may be determined using the tests described in the examples below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Materials. All chemicals were purchased from Sigma-Aldrich (St. Louis, Mo., USA) and used as received unless otherwise specified. Anhydrous dimethylformamide (DMF), ethyl acetate (EtOAc), and hexane were dried by passing them through alumina columns and kept anhydrous by storing them in the presence of molecular sieves in a glove box. Hexamethyldisilazane (HMDS) was dissolved in DMF in a glovebox. SiliaFlash P60 silica gel (particle size 40-63 μm) was purchased from SiliCycle Inc. (Quebec City, Quebec, Canada) and heated to 150° C. for 48 h before use. L-tert-butyl-Glu and DL-tert-butyl-Glu were purchased from Chem-impex International, INC. Spectra/Por® dialysis tubing with a molecular weight cut-off (MWCO) of 1 kDa was purchased from Spectrum Laboratories (Rancho Dominguez, Calif., USA). DH5c, MG1655 (*Escherichia coli*) were grown in luria broth (LB) medium at 37° C. *Helicobacter pylori* strain SS1, and clinical isolated strains, J68, J104, J166, J99, J99A-9, J99A-7, J99A-11, J99C-8 and J99D-1, supplied by Dr. Chen and Dr. Peek, were incubated in *brucella* broth (BB) with 10% fetal bovine serum (FBS) supplemented with vancomycin (5 μg/mL) in the incubation with the supplement of 10% carbon oxide at 37° C. Among them, J99A-7, J99A-11, J99C-8 and J99D-1 are drug resistant bacteria. All lipids were obtained from Avanti Polar Lipids, Inc. BacLight™ Kit L-7012 was purchased from Thermo Fisher Scientific Inc.

Instruments. $^1$H NMR spectra were recorded on a Varian U500 MHz or a VXR-500 MHz spectrometer. Chemical shifts were reported in ppm and referenced to the solvent proton impurities. Gel permeation chromatography (GPC) experiments were performed on a system equipped with an isocratic pump (Model 1100, Agilent Technology, Santa Clara, Calif., USA), a DAWN HELEOS multi-angle laser light scattering detector (MALLS) detector (Wyatt Technology, Santa Barbara, Calif., USA), and an OptilabrEX refractive index detector (Wyatt Technology, Santa Barbara, Calif., USA). The detection wavelength of HELEOS was set at 658 nm. Separations were performed using serially connected size exclusion columns (100 Å, 500 Å, 10$^3$ Å and 10$^4$ Å Phenogel columns, 5 μm, 300×7.8 mm, Phenomenex, Torrance, Calif., USA) at 60° C. using DMF containing 0.1 mol/L LiBr as the mobile phase.

The MALLS detector was calibrated using pure toluene and can be used for the determination of the absolute molecular weights (MWs). The MWs of polymers were determined based on the dn/dc value of each polymer sample calculated offline by using the internal calibration system processed by the ASTRA V software (version 5.1.7.3, Wyatt Technology, Santa Barbara, Calif., USA). Circular dichroism (CD) measurements were carried out on a JASCO J-815 CD spectrometer. The polymer samples were prepared at concentrations of 4.4 μM. The solution was placed in a quartz cell with a path length of 0.10 cm. The zeta-potential of polypeptides was evaluated by Malvern Zetasizer. Infrared spectra were recorded on a Perkin Elmer 100 serial FTIR spectrophotometer calibrated with polystyrene film. Lyophilization was performed on a FreeZonelyophilizer (Labconco, Kansas City, Mo., USA). UV light was generated from an OmiCure S1000 UV lamp (EXFO, Mississauga, Canada).

Animals. Female C57BL/6J mice were purchased from The Jackson Labs (Bai Harbor, Me., USA). Feed and water were available ad libitum. Artificial light was provided in a 12 h/12 h cycle.

Example 1. Monomer and Polypeptide Synthesis

Synthesis of L-tert-butyl-Glu-NCA (tBLG-NCA). A round-bottomed flask (100 mL) was charged with L-tert-butyl-Glu (3 g, 14.8 mmol) and dried under vacuum for 2 h. Anhydrous tetrahydrofuran (THF, 30 mL) and phosgene (15 wt % in toluene, 12.6 mL, 29.6 mmol) were added successively with the protection of nitrogen. The mixture was stirred at 50° C. for 2 h. The solvent was removed under vacuum to yield an oily liquid. The product was purified by silica gel column chromatography using EtOAC/hexane (from 100% to 50% hexanes) as the eluent (2.1 g, yield: 63%).

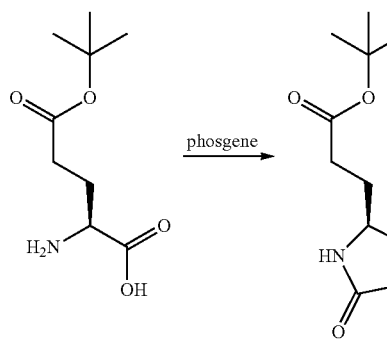

$^1$H NMR (CDCl$_3$, ppm): δ 6.70 (s, 1H, —NH), 4.39 (t, 1H, —CHNH), 2.48 (t, 2H, —CH$_2$CH$_2$COO—), 2.25-2.06 (m, 2H, —CH$_2$CH$_2$COO—), 1.46 (s, 9H, C(CH$_3$)$_3$). $^{13}$C NMR (CDCl$_3$, ppm): δ 172.3, 169.8, 152.6, 82.2, 57.5, 31.5, 28.3, 27.2.

tBDLG-NCA was synthesized similarly using tBDLG as the starting material (Yield: 71%). $^1$H NMR (CDCl$_3$, ppm): δ 6.82 (s, 1H, —NH), 4.37 (t, 1H, —CHNH), 2.47 (t, 2H, —CH$_2$CH$_2$COO—), 2.26-2.06 (m, 2H, —CH$_2$CH$_2$COO—), 1.46 (s, 9H, C(CH$_3$)$_3$). $^{13}$C NMR (CDCl$_3$, ppm): δ 172.4, 169.8, 151.8, 82.3, 57.6, 31.6, 28.3, 27.3.

Synthesis of random copolymers poly(γ-6-chlorohexyl-L-glutamate)-r-poly(tert-butyl-L-Glu) (PCHLG-r-PtBLG). L-γ-(6-chlorohexyl)-Glu-NCA (CH-L-Glu-NCA) were synthesized according to our previous work (Xiong et al. (2015) Proc Natl Acad Sci USA 112:13155-13160). In the glovebox, CH-L-glu-NCA, L-tert-butyl-Glu and HMDS was mixed in various feeding molar ratios (20:20:1) and dissolved in DMF (1.5 mL). The mixture was stirred at room temperature for 48 h. The polymers were then precipitated in cold ether/hexane (v/v=1:1) and dried under vacuum at 40° C. for 8 h. Poly(γ-6-chlorohexyl-DL-glutamate)-r-poly(DL-tert-butyl-Glu) (PCHDLG-r-PtBDLG) was synthesized by with the same method using CH-DL-glu-NCA and DL-tert-butyl-Glu as the monomers with a feeding molar ratio at 20:20 (M/I=40).

Synthesis of antibacterial polypeptides. PL1 was synthesized according to our previous study (Xiong et al. (2015) Proc Natl Acad Sci USA 112:13155-13160) (Scheme 1; Scheme 2).

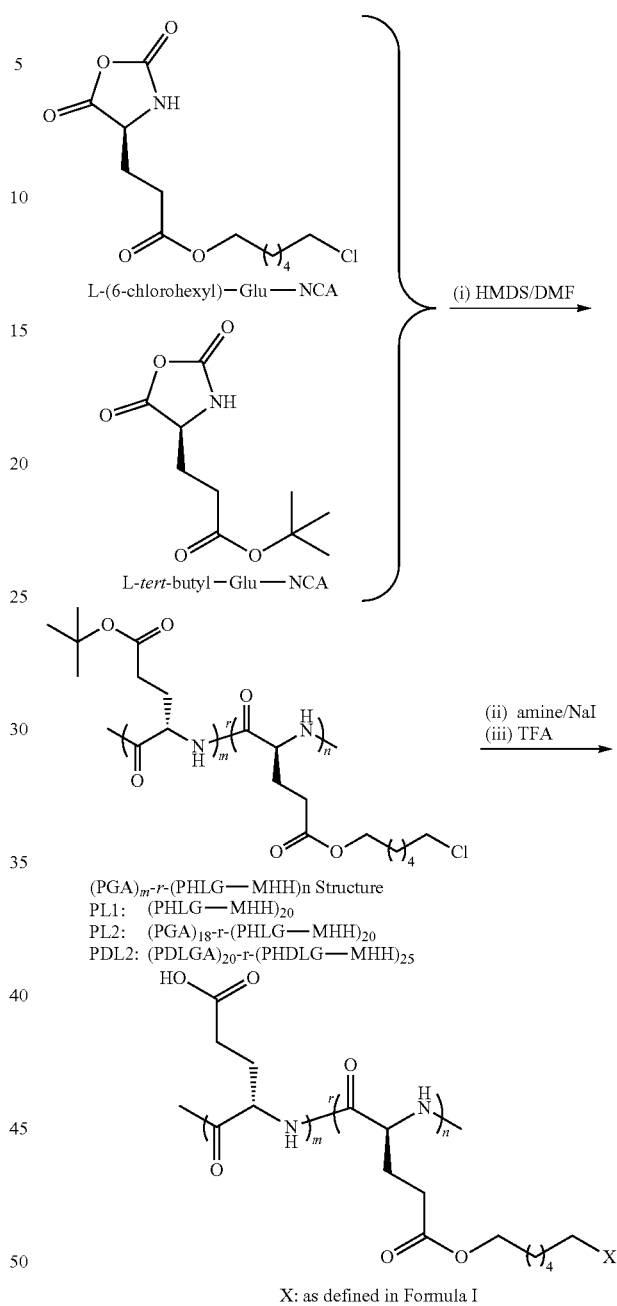

PL2, and PDL2 were synthesized using PCHLG$_{20}$-r-PtBLG$_{18}$ and PCHDLG$_{25}$-r-PtBDLG$_{20}$, respectively, to react with amines such as N-methyldihexylamine ("amine" or X in Schemes 1 and 2). The tert-butyl groups were removed by trifluoroacetic acid (TFA). Briefly, the polypeptides were dissolved in DMF (2 mL), NaI (3 equiv of chloro groups) was dissolved in acetonitrile (2 mL). The mixture was transferred to a 25 mL Schlenk tube into which N-methyldihexylamine (3 equiv of chloro groups) was added. The mixture was stirred at 80° C. for 48 h. After most solvent was removed under vacuum, NaCl aqueous solution (1.0 M, 3 mL) was added. The solution was stirred at room temperature for 3 h to promote ion exchange. PHLG-MHH$_{20}$-r-PtBLG$_{18}$ and PHDLG-MHH$_{25}$-r-PtBDLG$_{20}$ were then obtained after purification by dialysis (MWCO=1 kDa) against distilled water for 1 days and lyophilization. The polypeptides were then dissolved in TFA/methylene (1:3, v/v) and stirred for 3 h under room temperature. The PL2 and PDL2 were then obtained after purification by dialysis (MWCO=1 kDa) against distilled water for 1 days and lyophilization.

Cy5 labeled PL2 and PDL2 were synthesized as shown in Scheme 3. Briefly, PCHLG$_{20}$-r-PtBLG$_{18}$ and PCHDLG$_{25}$-r-PtBDLG$_{20}$ were first react with 3-azido-N,N-dimethylpropan-1-amine (0.2 equiv of chloro groups) and NaI (3 equiv of chloro groups) for one day, and then N-methyldihexylamine (3 equiv of chloro groups) were added. The mixture was stirred for another two days under 80° C. The polypeptides were obtained after purification by dialysis (MWCO=1 kDa) against distilled water for 1 days and lyophilization, followed by de-esterification using TFA.

Scheme 3. Synthetic route of cy5 labeled PL2.

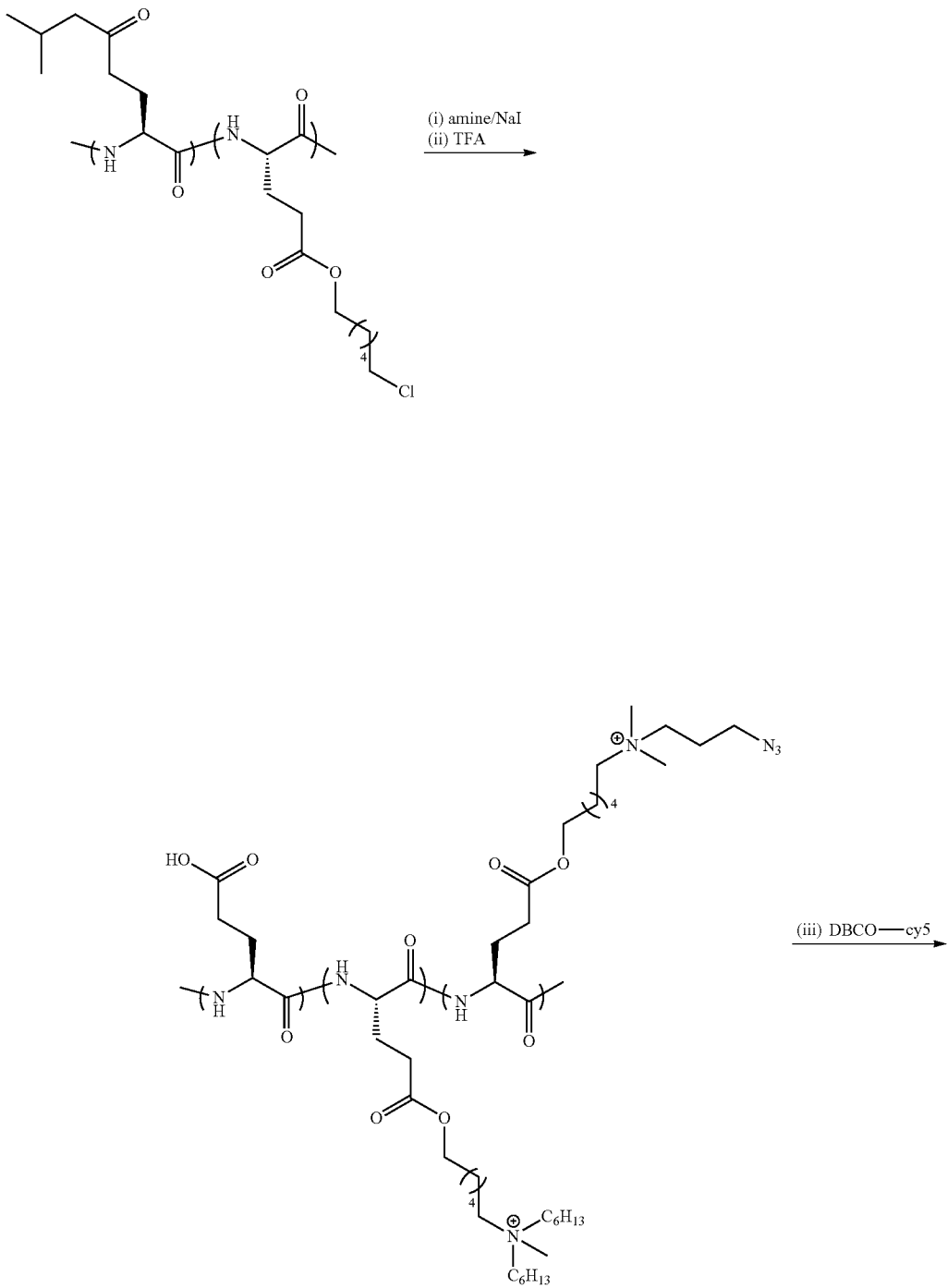

-continued

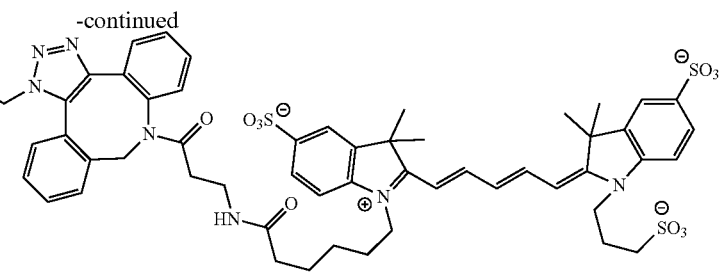
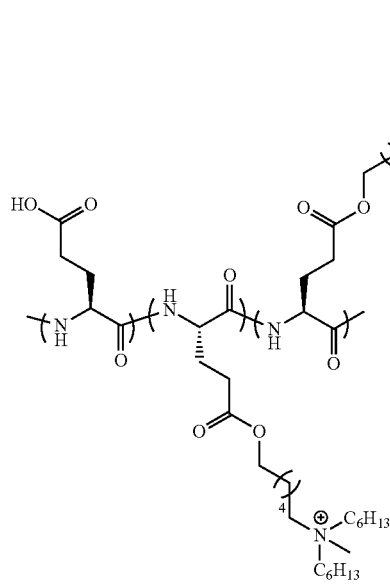

Figure 10:
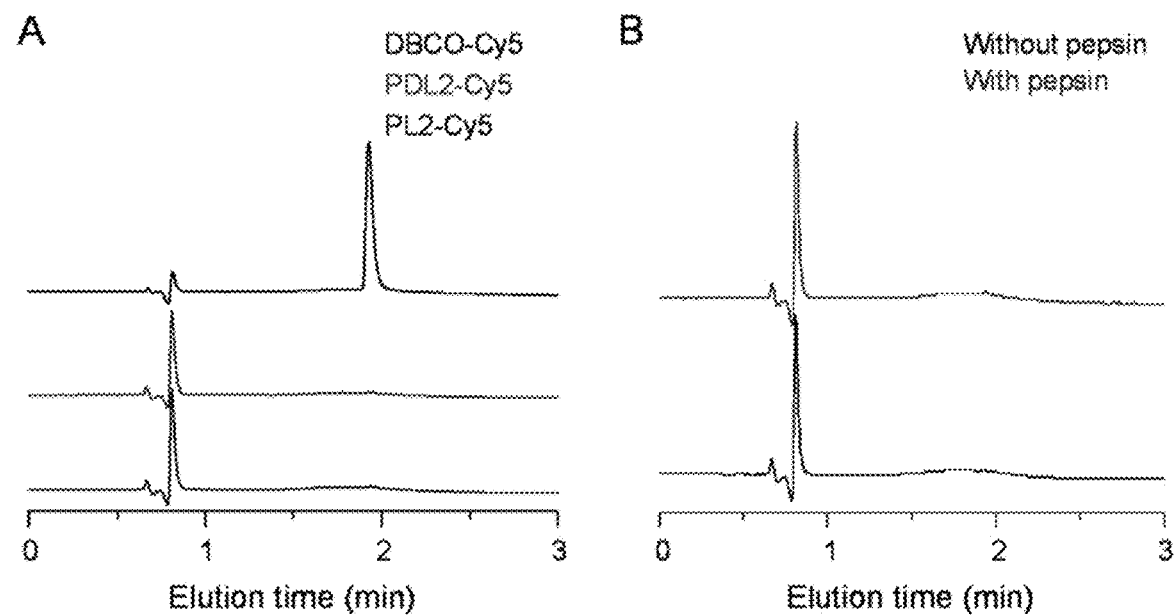
FIG. 10. (A) HPLC analysis of Cy5-PL2 and PDL2-cy5. (B) The stability of Cy5-PL2 against pepsin after 24 h incubation.
Figure 11:
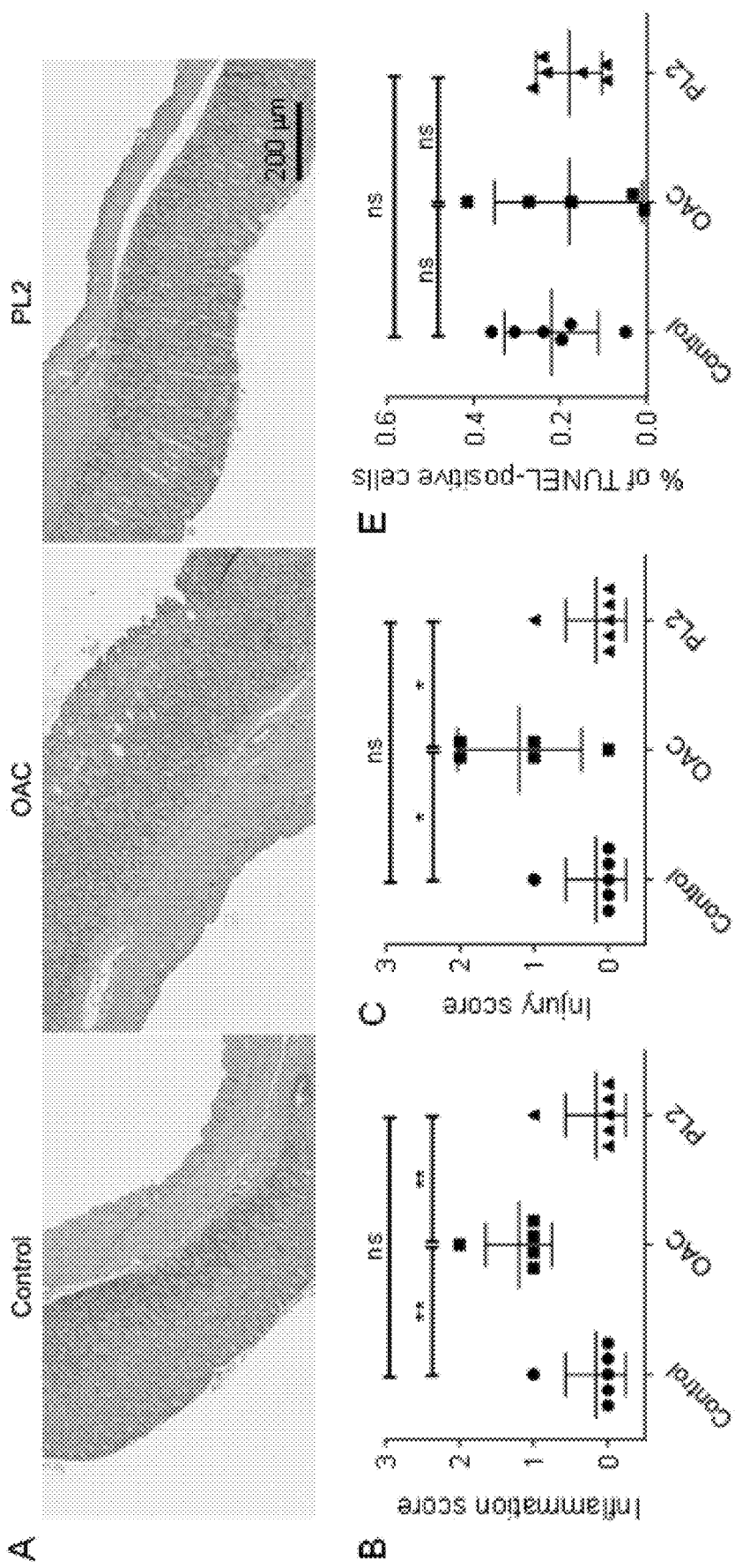
FIG. 11. Toxicity of PL2 towards mouse stomach after gavage. (A) Representative images of H&E stained stomach from mice receiving control, OAC and PL2 treatments (n≥5, scale bar=200 µm). The inflammation score (B) and injury score (C) of stomach according to the images of H&E staining. (D) Representative TUNEL straining images of mouse stomach from mice receiving control, OAC and PL2 treatments (n≥5, scale bar=200 µm). (E) The percentage of positive cells as calculated from TUNEL staining images. At least 10 different images of 200× area were randomly selected for each tissue to count the apoptotic cell percentage (mean±SD, n≥5). The relative activity of caspase 3 (F) and caspase 8 (G) of the stomach after control, OAC, and PL2 treatments. The average activity of caspase 3/8 of control mice was set as 100%. Inflammation was graded on a 0-3 ordinal scale based on the Sydney System as follows: chronic inflammation (mononuclear cell infiltration independent of lymphoid follicles); grade 0, no inflammation; grade 1, mild inflammation (slight increase in mononuclear cells); grade 2, moderate inflammation (dense but focal mononuclear inflammatory cells); and grade 3, severe inflammation (dense and diffuse mononuclear inflammatory cells). The appearance of the mucosa was graded as follows.
Figure 11:
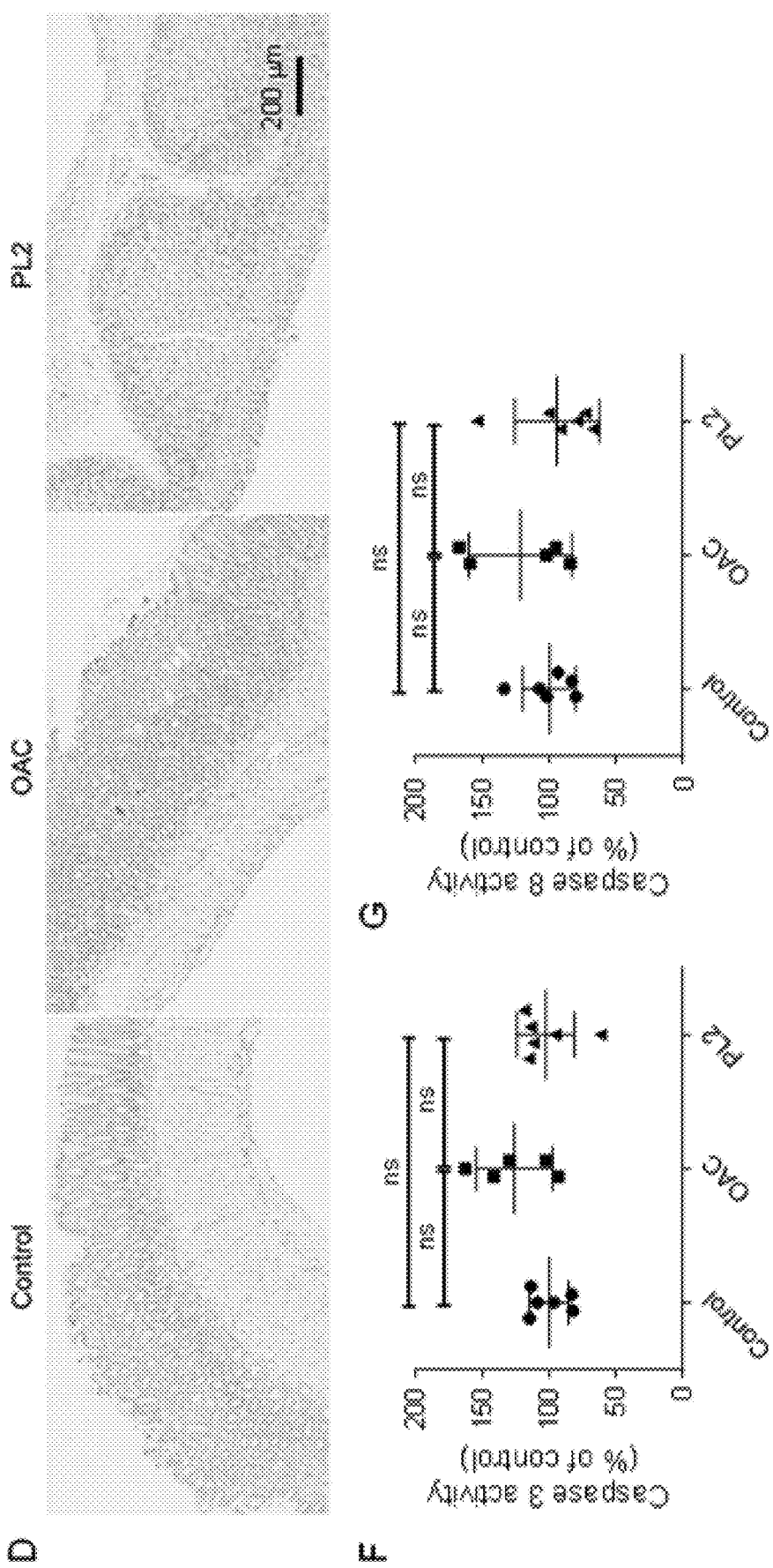

Cy5 labeled polypeptides were obtained by incubation with DBCO-cy5 (0.5 equiv of azido groups) in dimethyl sulfoxide/H2O (v/v=1:1). The conversion of DBCO-cy5 were complete after 24 h incubation, confirmed by HPLC (FIG. 10).

Example 2. Biological Assays and Therapeutic Characterizations

Minimal inhibition concentration (MIC). Gram-negative bacteria, DH5α and MG1655 (*E. coli*) were grown in LB medium at 37° C. For determination of the MIC, polypeptides were dissolved in media using serial dilutions from a stock solution. Into each well of a 96-well plate was added 200 μL of each concentration and 2 μL of bacteria (1×10$^8$ CFU (colony forming units)) in medium. The plate was incubated at 37° C. The optical density readings of microorganism solutions were measured after 24 h incubation. The MIC was considered as the lowest concentration of peptide where no visual growth of bacteria was detected.

*H. pylori* killing kinetics at various pHs. The killing kinetics of polypeptides were measured against *H. pylori* by counting the colony forming units (CFU) of alive bacteria with agar plating. The polypeptides at various concentrations were dissolved in the Tris-HC buffer at various pHs (pH 7.4, 4.0, 3.0). *H. pylori* were then collected and dispersed in the BB medium supplied with fresh urea (10 mM) and 10% FBS at different pHs (pH 7.4, 4.0, 3.0). The optical density at 600 nm of the bacteria were fixed at 0.1. The bacteria were then incubated with the polypeptides solution at corresponding pH in the incubator supplied with 10% $CO_2$ at 37° C. Samples were taken for a series of ten-fold dilutions, and plated out in BB agar plates with 10% FBS and vancomycin (pH 7.4) after 1 h incubation. The plates were incubated for 72 h in the incubator and the bacteria were counted for CFU. Bacteria incubated with Tris-HCl buffer only at corresponding pH were served as 100% survival. Survival rate (%)=CFU of bacteria treated with polypeptides/CFU of bacteria treated with buffer×100%.

The killing kinetics of antibiotics (OAC, omeprazole, amoxicillin, clarithromycin) against *H. pylori* were determined with a similar procedure. The antibiotics at various concentrations were dissolved in the Tris-HCl buffer at pH 7.4, or 3.0, and were then incubated with *H. pylori* in BB medium supplied with fresh urea (10 mM) and 10% FBS at corresponding pH in the incubator. After 1 h incubation, the bacteria were collected by centrifuge at 10,000 rcf for 5 min and washed with fresh BB medium. Samples were then taken for a series of ten-fold dilutions, and plated out in BB agar plates with 10% FBS and vancomycin. The plates were incubated for 72 h in the incubator and the bacteria were counted for CFU.

Hemolytic assay. Fresh rabbit blood was obtained and subjected to 25-fold dilution with PBS buffer to reach a concentration of approximately 4% (in volume) of the blood cells. 300 μL of PBS solution containing a polypeptide at various concentrations was placed in a 1.5 mL microfuge tube, followed by the addition of an equal volume (300 μL) of red blood cell suspension. The mixture was incubated at 37° C. for 1 h to allow for the hemolysis process to take place. At the end of the incubation time, the non-hemolysed red blood cells were separated by centrifugation at 1000 rpm for 5 min. Aliquots (100 μL) of the supernatant were transferred to a 96-well plate, and hemoglobin release was measured by UV-absorbance at 576 nm using a microplate reader (TECAN, Switzerland). Two controls were provided in this assay: an untreated red blood cell suspension in PBS solution was used as the negative control; a solution containing red blood cells lysed with 1% Triton-X was used as the positive control. Percentage of hemolysis was calculated using the following formula: Hemolysis (%)=[(O.D. 576 nm of the treated sample–O.D. 576 nm of the negative control)/(O.D. 576 nm of positive control–O.D. 576 nm of negative control)]×100%.

The stability of polypeptides against pepsin. Cy5 labeled PL2 (1.0 mg/mL) was incubated with pepsin (1.0 mg/mL) in Tris buffer (pH 4.0) at 37° C. After 24 h of incubation, the samples were taken out for HPLC analyses.

Fluorescence microscopy of stained bacterial cells. A Zeiss XBO 75 Fluorescence Microscope (Carl Zeiss) was used for fluorescence studies. A BacLight™ Kit L-7012 was used as the fluorescence dye: SYTO9 to examine bacteria in the presence of polypeptides. It is important to mention that an initial bacterial concentration of ~10$^{18}$ cells/mL was used for microscopy for ease of visualization. SYTO9 and cy5 labeled PL2 (2.2 µM) were incubated with SS1 under pH 7.4 and pH 4.0 with the presence of urea (10 mM). Solution of cells, dye, and polymer were allowed to stand for 30 min, and 50 µL of the solution was placed on a slide, mounted with a coverslip, and visualized under fluorescence microscope.

Liposome dye leakage assay. ANTS (12.5 mM) and DPX (45 mM) were dissolved in Tris buffer (pH=7.4). To a clean round-bottom flask, appropriate volumes of lipid stocks were added to make up 1 mL of $CHCl_3$ (3:1 POPE (1-palmitoyl-2-oleoyl-sn-glycero-3-phosphoethanolamine)/POPG (1-palmitoyl-2-oleoyl-sn-glycero-3-phospho-(1'-rac-glycerol) (sodium salt)) vesicles, POPE (130 µL, 25 mg/mL $CHCl_3$) and POPG (115 µL, 10 mg/mL $CHCl_3$) were used). The solvent was removed by a stream of nitrogen gas to obtain a thin lipid film, which was then hydrated by 1 mL of ANTS/DPX solution. The mixture was left to hydrate for 1 h, after which it was subjected to 10 freeze-thaw cycles (using dry ice/acetone to freeze and warm water to thaw). The suspension was extruded 20 times through a polycarbonate membrane with 400 nm pore diameter. The excess dye was removed using Sephadex G-50 column as the eluent. The dye-filled vesicle fractions were diluted 200 times with Tris buffer. This suspension (90 µL) was subsequently mixed with polypeptide stock solutions (10 µL) at various pH (pH 7.4 or 4.0) on a 96-well black microplate (Greiner, flat bottom). Tris buffer (10 µL, pH 7.4 or 4.0) and Triton-X (0.1% v/v, 10 µL, pH 7.4 or 4.0) were employed as the negative and positive controls at corresponding pH, respectively. After 30 min, the fluorescence intensity in each well was recorded using the microplate reader with excitation and emission wavelengths of 380 and 520 nm, respectively. The percentage of leaked calcein dye in each well was determined as follows: leakage $(\%)=[(F-F_0)/(F_{TX}-F_0)]\times 100\%$, where F is the fluorescence intensity recorded in the well, $F_0$ is the intensity in the negative control well, and $F_{TX}$ is the intensity in the positive control well.

SEM analysis. SS1 bacterial cells grown in BB with the supplement of 10% FBS under pH 7.4 or 4.0 with or without polypeptides (2.2 µM) treatment were performed using a similar protocol as killing kinetics measurements but with a 30 min incubation time. All the samples were collected into a microfuge tube and pelleted at 4000 rpm for 5 min, and then washed twice with phosphate-buffered saline. Subsequently, bacteria were fixed with paraformaldehyde solution (4%) for 1 h before proceeding, followed by washing with DI water. Dehydration was performed with a series of graded ethanol solution (10%, 25%, 50%, 75%, 95%, and 100%). The dehydrated samples were dried under vacuum overnight before being mounted on carbon tape and coated with gold-platinum for imaging using a Hitachi S-4700 High Solution SEM (Japan).

In vivo and ex vivo biodistribution of Cy5-PL2. Cy5-PL2 (2.6 µmol/kg), Cy5-PDL2 (2.6 µmol/kg) and PBS were administrated by oral gavage. Mice were placed on the sample stage equipped with anesthesia input and output ports, and imaged by the Bruker Xtreme In-Vivo Fluorescence Imaging System at 1 h, 2 h, 4 h, 7 h, and 24 h post injection (p.i.). The excitation filter was set at 630 nm and the emission filter was set at 700 nm. Collected images were analyzed by the Bruker molecular imaging software. Stomach, intestines, liver, lung, kidneys, heart, and spleen were harvested at 4 h or 24 h p.i. of Cy5-PL2 and imaged ex vivo using the Bruker Xtreme In-Vivo Imaging System. Ex vivo images were quantified by measuring FI at selected region of interest (ROI). All values were expressed as means±standard deviation (n=3). After ex vivo imaging, stomachs were bisected. Half of the stomach was directly frozen in O.C.T. compound and sectioned on a cryostat (Leica CM3050S) with a thickness of 6 µm. Hoester solution (2 µg/mL) was added to stain cell nucleus. After multiple washing steps, coverslips were mounted onto the microscope slides with the addition of ProLong Gold antifade reagent, and the prepared samples were stored in the dark for confocal imaging. The other half of the stomach were placed into separate glass tubes containing 2 mL of lysis buffer (1% SDS, 100 10 mM Tris.HCl, pH 7.4, 1 tablet of EDTA-free protease inhibitor), homogenized, and incubated at 4° C. for 2 h. The lysates were then centrifuged at 3000 rcf for 10 min to remove the insoluble cell debris, and measured on a fluorescence spectrometer to determine the amount of Cy5 retained in the tissues. The amount of Cy5 was calculated based on the standard curve of Cy5 FI and normalized to percentage of injected dose (% I.D.) per gram tissue.

Anti-*H. pylori* efficacy in vivo. Each C57BL/6J mouse received 0.2 mL *H. pylori* SS1 ($OD_{600}=2$) in BHI broth administered intragastrically through oral gavage every other day for four times (on days 1, 3, 5 and 7, respectively), and the infection was allowed to develop for 2 wk. The mice were randomly assigned to four treatment groups (n≥6) to receive PL2, PDL2, triple therapy (omeprazole, amoxicillin, clarithromycin), or PBS. For triple therapy, mice were first administered omeprazole (a proton pump inhibitor) through oral gavage at a dose of 400 µmol/kg, followed by a lag time of 30 min before administration of amoxicillin (68.0 µmol/kg) and clarithromycin (19.1 µmol/kg). PL2 and PDL2 in 5% (vol/vol) DMSO (both at 2.6 µmol/kg) were administered through oral gavage once daily for a consecutive 3 d. Water solution with 5% DMSO was served as negative control group. Forty-eight hours after the last administration, mice were killed and the stomach was removed from the abdominal cavity. The stomach was cut along the greater curvature, and the gastric content was removed and rinsed with PBS. The stomach sections were used for assessment of bacterial colonization. For bacterial colonization, a gastric tissue section was suspended in 1 mL PBS and homogenized for *H. pylori* recovery. The homogenate was serially diluted and spotted onto Columbia agar plate containing vancomycin (20 µg/mL), amphotericin (2 µg/mL), bacitracin (30 µg/mL) and nalidixic acid (10 µg/mL). The plates were then incubated at 37° C. under microaerobic conditions for 5 d, and bacterial colonies were enumerated and adjusted for dilutions.

Toxicity of PL2 in vivo. Mice were given a daily gavage of PL2 (2.6 µmol/kg), 5% DMSO, OAC and physiological saline for 3 consecutive days. Mice were sacrificed on day 5, and the blood samples were collected for the analysis of alanine aminotransferase (ALT), aspartate aminotransferase (AST), creatinine, urea nitrogen, sodium ion and potassium ion levels. The colonic segment, stomach, liver, small intestine, kidney and feces of each mouse was gathered and homogenized with cold PBS (pH7.4). The stomachs were used to determine the expression of caspase 3 and caspase 8 using Caspase 3 Assay Kit (Sigma) and Caspase 8/FLICE Colorimetric Kit (Life technology), respectively. The colonic segment and feces were used to extract bacterial DNA. The stomach, small intestine, liver, and kidney were kept in formalin for H&E staining. The stomachs were also kept in formalin for terminal deoxynucleotidyl transferase dUTP nick end labeling (TUNEL) assay (S7100|ApopTag® Peroxidase In Situ Apoptosis Detection Kit). The percentage of TUNEL positive cells in the stomach after control, OAC, PL2 treatments were counted from 10 different images (mean±SD, n≥5).

The inflammation and injury of stomach were scored by Dr. Liu in a blind manner based on the H&E staining. Inflammation was graded on a 0-3 ordinal scale based on the Sydney System as follows: chronic inflammation (mononuclear cell infiltration independent of lymphoid follicles); grade 0, no inflammation; grade 1, mild inflammation (slight increase in mononuclear cells); grade 2, moderate inflammation (dense but focal mononuclear inflammatory cells); and grade 3, severe inflammation (dense and diffuse mononuclear inflammatory cells). The appearance of the mucosa was graded as follows: 0, normal; 1, spotty changes in cellular staining characteristics of some surface epithelial cells in an otherwise normal mucosa (mild injury); 2, more generalized changes and/or disruption of the surface epithelium in several areas (moderate injury); 3, extensive mucosal destruction (severe injury).

The killing effect of PL2 against commensal bacteria was determined by measuring the bacterial load in the feces and ileal contents of mice after a daily gavage of PL2 (2.6 µmol/kg in 5% DMSO), 5% DMSO and OAC for 3 consecutive days. The bacterial load was determined by quantitative real-time PCR using a protocol modified from Stefka et al., and Buffie et al. (Stefka et al. (2014) Commensal bacteria protect against food allergen sensitization. *Proc Natl Acad Sci USA* 111:13145-13150; Buffie et al. (2012) Profound alterations of intestinal microbiota following a single dose of clindamycin results in sustained susceptibility to *Clostridium difficile*-induced colitis. *Infect Immun* 80:62-73). Fecal DNA was extracted as for sequencing, and bacterial load was quantified against a standard curve derived from apCR4TOPO-TA vector containing a nearly full-length copy of the 16S rRNA gene from a member of Porphyromonadaceae. Bacterial DNA was amplified with universal primers 8F and 338R using the iQ SYBR greensupermix (Bio-RadLifeScience) and the StepOne Plus system (AppliedBiosystems). The results were normalized to ileal content/fecal weight.

Statistical analysis. The statistical analysis was performed by one-way analysis of variance (ANOVA) with post hoc Fisher's Least Significant Difference (LSD) test (OriginPro 8.5) or Student's t-test (two-tailed) comparisons at 95% confidence interval. The results were deemed significant at $*P \leq 0.05$.

Example 3. Pharmaceutical Dosage Forms

The following formulations illustrate representative pharmaceutical dosage forms that may be used for the therapeutic or prophylactic administration of a polypeptide of a formula described herein, a polypeptide specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcry sialline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An antimicrobial random polypeptide comprising Formula I:
wherein

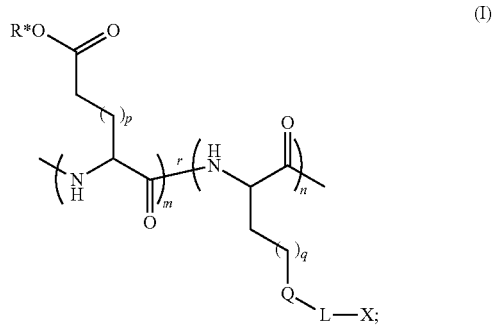

m is 3 to about 50;

n is 5 to about 100;

p is 0 to 10;

q is 0, 1, 2, or 3;

R* is H or a negative charge;

Q is —C(=O)O—, —C(=O)NH—, —NH—C(=O)—, or a direct bond;

L is a carbon-containing linker of at least two atoms in length; and

X is —N$^+$(R)$_3$ wherein each R is independently phenyl or a straight chain or branched (C$_1$-C$_{10}$)alkyl;

wherein the random polypeptide adopts a random coil confirmation in solution at a pH of greater than about 6.5, and the random polypeptide adopts a helical confirmation in solution at a pH of less than about 3.5; and the term, about, refers to a variation of ±10% of the value it modifies.

2. The polypeptide of claim 1 wherein L is (C$_2$-C$_{12}$)alkyl, wherein the (C$_2$-C$_{12}$)alkyl is optionally interrupted with one to five oxygen atoms, sulfur atoms, or a combination thereof, and optionally interrupted with phenyl, cycloalkyl, heterocycle, or heteroaryl.

3. The polypeptide of claim 1 wherein the total number of carbon atoms in the three R groups combined is 3 to about 15.

4. The polypeptide of claim 3 wherein X is:

wherein X is bonded to L at the nitrogen of X to form a quaternary ammonium moiety.

5. The polypeptide of claim 1 wherein the polypeptide comprises Formula V:

(V)

wherein m is about 3 to about 40, n is about 5 to about 80, t is about 1 to 8, and R$^1$ and R$^2$ are each independently (C$_2$-C$_8$)alkyl.

6. The polypeptide of claim 1 wherein L is (C$_2$-C$_{12}$)alkyl, —CH$_2$-Ph-(CH$_2$)$_y$— wherein y is 1 to about 4, —CH$_2$-Ph-O—(CH$_2$)$_2$—O—(CH$_2$)$_2$—, —CH$_2$-Ph-O—(CH$_2$)$_2$—S—(CH$_2$)$_2$—, —CH$_2$-Ph-O—(CH$_2$)$_3$—O—(CH$_2$)$_2$—, —CH$_2$-Ph-O—(CH$_2$)$_3$—S—(CH$_2$)$_2$—, or —CH$_2$-Ph-O—CH$_2$—CH(S(CH$_2$)$_2$—X)—CH$_2$—S—(CH$_2$)$_2$—.

7. The polypeptide of claim 1 wherein the polypeptide at a concentration of about 4.4 µM has high antibacterial activity against *H. pylori* in an environment having a pH of about 3 wherein less than 10% of *H. pylori* survive in the presence of said concentration of the polypeptide at said pH.

8. A random polypeptide comprising Formula II:
wherein (II)

m is 3 to about 50;

n is 5 to about 100;

p is 0 to 10;

q is 0, 1, 2, or 3;

R* is H or a negative charge;

Q is —C(=O)O—, —C(=O)NH—, —NH—C(=O)—, or a direct bond;

L is a carbon-containing linker of two to twenty atoms in length; and

X is an aliphatic quaternary ammonium moiety or aromatic quaternary ammonium moiety;

wherein the term, about, refers to a variation of ±10% of the value it modifies.

9. The polypeptide of claim 8 wherein the aromatic quaternary ammonium moiety is selected from:

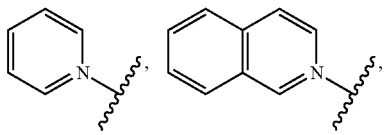

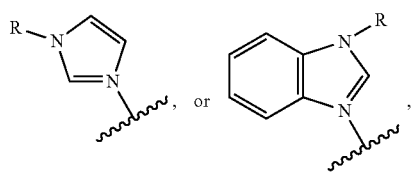

wherein R is H or (C₁-C₁₀)alkyl.

10. The polypeptide of claim 8 wherein the polypeptide comprises Formula III or Formula IV:

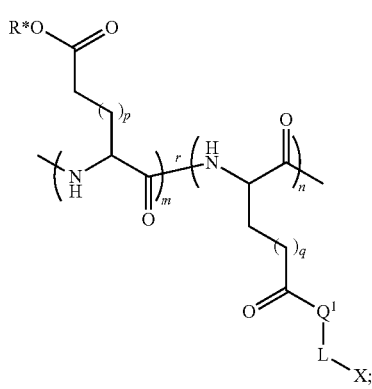

(III)

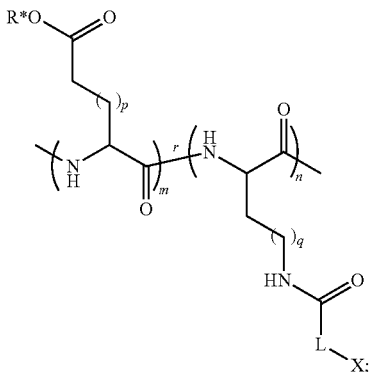

(IV)

wherein Q¹ is O or NH.

11. A random polypeptide comprising (PL2):

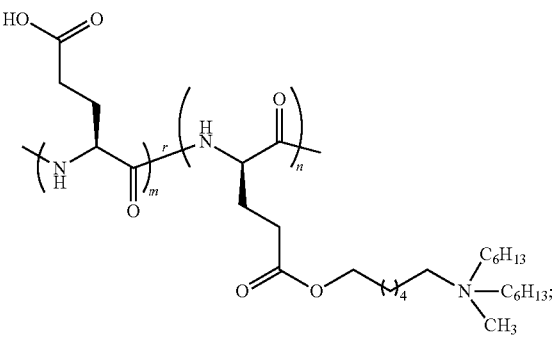

(PL2)

wherein m is 3 to 40±10%; and n is 5 to 80±10%.

12. The polypeptide of claim 1 wherein m is about 18 and n is about 20.

13. A method comprising treating a bacterial infection in the stomach of a subject in need thereof by administering to the subject a therapeutically effective amount of a polypeptide of claim 1, wherein the bacterial infection is thereby treated.

14. The method of claim 13 wherein the polypeptide is administered orally.

15. The method of claim 14 wherein the bacterial infection is caused by *H. pylori*.

16. The method of claim 15 wherein the subject has been diagnosed with gastritis, or a gastric ulcer.

17. The method of claim 13 wherein the polypeptide causes killing of less than 50% of commensal bacteria in the ileal contents.

* * * * *